Figure 1:
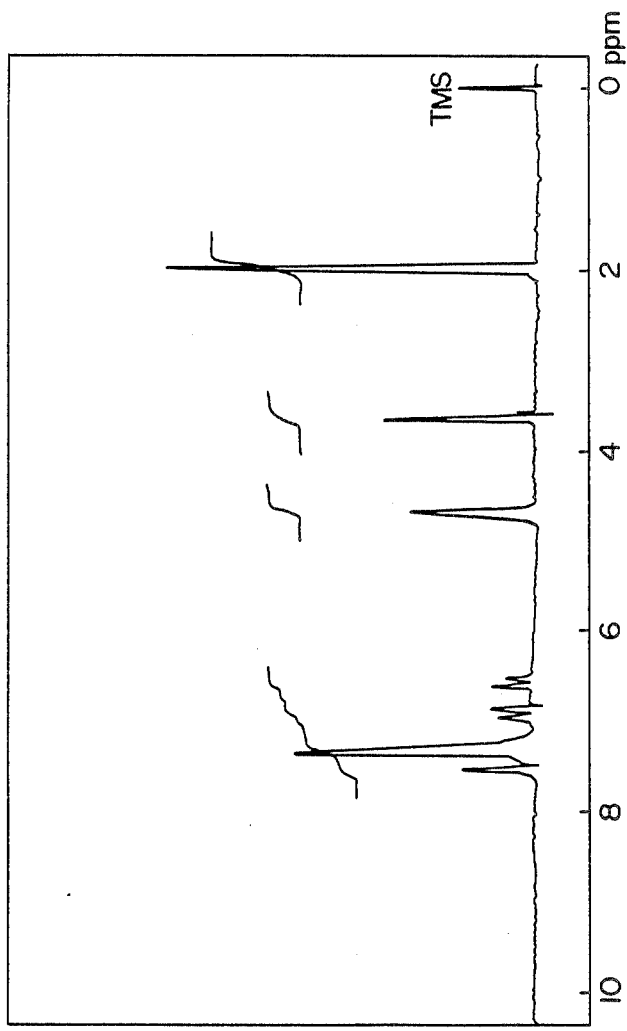

United States Patent [19]

Takematsu et al.

[11] Patent Number: 4,802,907
[45] Date of Patent: Feb. 7, 1989

[54] N-SUBSTITUTED CHLOROACETANILIDES PROCESSES FOR PRODUCTION THEREOF, AND HERBICIDAL COMPOSITION COMPRISING THE SAME

[75] Inventors: Tetsuo Takematsu, Utsunomiya; Shozo Kato, Fujisawa; Masahiko Ishizaki, Sagamihara; Toshihisa Suyama, Chigasaki, all of Japan

[73] Assignee: Tokuyama Soda Kabushiki Kaisha, Yamaguchi, Japan

[21] Appl. No.: 94,092

[22] Filed: Sep. 4, 1987

Related U.S. Application Data

[63] Continuation of Ser. No. 622,649, Jun. 20, 1984, abandoned.

[30] Foreign Application Priority Data

Jun. 22, 1983 [JP] Japan ................. 58-111011

[51] Int. Cl.⁴ .............. A01N 43/02; C07D 333/32
[52] U.S. Cl. ............................... 71/90; 549/65
[58] Field of Search ................ 549/65, 77; 71/90

[56] References Cited

U.S. PATENT DOCUMENTS 3,901,917 8/1975 Richter et al. ................ 549/74

FOREIGN PATENT DOCUMENTS 24194 2/1980 Japan .

*Primary Examiner*—Alan Siegel
*Attorney, Agent, or Firm*—Sherman and Shalloway

[57] ABSTRACT

An N-substituted chloroacetanilide represented by the following formula (I)

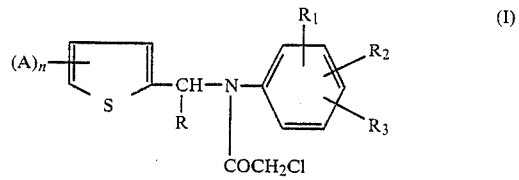

wherein A represents a member selected from the class consisting of halogen atoms, alkoxy groups having a linear or branched, saturated or unsaturated $C_1$–$C_6$ alkyl group, alkylthio groups having a linear or branched, saturated or unsaturated $C_1$–$C_6$ alkyl group, and alkoxyalkyl groups having a linear or branched, saturated or unsaturated $C_1$–$C_6$ alkyl group and having a linear or branched, saturated or unsaturated $C_1$–$C_6$ alkylene group, $R_1$, $R_2$ and $R_3$ are identical or different, and each represents a hydrogen atom, a halogen atom, a linear or branched, saturated or unsaturated $C_1$–$C_6$ alkyl group, an alkoxy group having a linear or branched, saturated or unsaturated $C_1$–$C_6$ alkyl group R is a hydrogen atom or a linear or branched, saturated or unsaturated $C_1$–$C_4$ alkyl group, or an alkylthio group having a linear or branched, saturated or unsaturated $C_1$–$C_6$ alkyl group, and n represents 1 or 2, and when n is 2, the two A's may be identical or different; a process for producing the above compound by reacting an N-substituted aniline with a chloroacetyl halogenide or by reacting a 2-substituted thiophene with a chloroacetanilide; and a herbicidal composition containing a herbicidally effective amount of the compound of formula (I).

4 Claims, 5 Drawing Sheets

N-SUBSTITUTED CHLOROACETANILIDES PROCESSES FOR PRODUCTION THEREOF, AND HERBICIDAL COMPOSITION COMPRISING THE SAME

This application is a continuation of application Ser. No. 622,649, filed June 20, 1984, now abandoned.

This invention relates to N-substituted chloroacetanilides not described in the known literature. Ths invention also relates to a process for producing the N-substituted chloroacetanilides, and a herbicidal composition comprising such a novel compound which has an outstanding control efficacy on paddy weeds.

More specifically, this invention relates to N-substituted chloroacetanilides represented by the following formula (I)

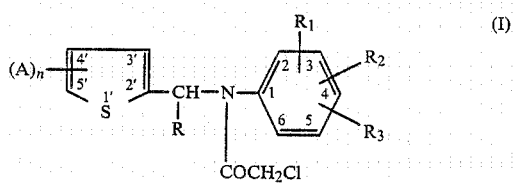

wherein

A represents a member selected from the class consisting of halogen atoms, alkoxy groups having a linear or branched, saturated or unsaturated $C_1$–$C_6$ alkyl group, alkylthio groups having a linear or branched, saturated or unsaturated $C_1$–$C_6$ alkyl group, and alkoxyalkyl groups having a linear or branched, saturated or unsaturated $C_1$–$C_6$ alkyl group and having a linear or branched, saturated or unsaturated $C_1$–$C_6$ alkylene group R is a hydrogen atom or a linear or branched, saturated or unsaturated $C_1$–$C_4$ alkyl group, $R_1$, $R_2$ and $R_3$ are identical or different, and each represents a hydrogen atom, a halogen atom, a linear or branched, saturated or unsaturated $C_1$–$C_6$ alkyl group, an alkoxy group having a linear or branched, saturated or unsaturated $C_1$–$C_6$ alkyl group, or an alkylthio group having a linear or branched, saturated or unsaturated $C_1$–$C_6$ alkyl group, and n represents 1 or 2, and when n is 2, the two A's may be identical or different.

This invention also pertains a process for producing the compounds of formula (I), and a herbidical composition comprising the compound of formula (I) as an active ingredient, particularly effective against paddy weeds.

Some compounds within the category of the N-substituted chloroacetanilides have previously been proposed, and it is known that some of these compounds are useful as herbicides.

For example, U.S. Pat. No. 3,901,917, issued on Aug. 26, 1975, discloses compounds of the following formula useful as herbicides and a process for production thereof.

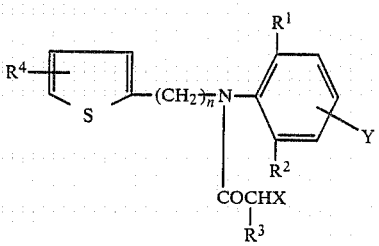

In the above formula, $R^1$ is lower alkyl, $R^2$ is selected from the group consisting of hydrogen, lower alkyl and lower alkoxy, Y is selected from the group consisting of hydrogen, lower alkyl and halogen, $R^3$ and $R^4$ are independently selected from the group consisting of hydrogen and lower alkyl, n is an integer of 1 or 2, and X is halogen. The U.S. patent does not at all describe or suggest compounds having the substituent A defined in the compounds of the present invention represented by formula (I), as can be seen from the definition of $R^4$ above.

The U.S. patent shows the results of pre-emergence pot tests of N-(2-thienylmethylene)-2,6-dimethyl-alpha-chloroacetanilide (Example 3) and N-(2-thienylmethylene)-2,6-diethyl-alpha-chloroacetanilide under upland farm conditions. It is apparent to those skilled in the art from these test results that the effective concentrations of the compounds as herbicides specifically disclosed in this patent document are about 10 pounds/acre, that is, about 1130 g/10a, although varying slightly depending upon the kinds of weeds, and their practical herbidical efficacy is difficult to achieve unless they are applied in very high dosages. In addition, this U.S. patent does not at all refer to the utility of the compounds disclosed there as herbicides for rice cultivation.

Japanese Laid-Open Patent Publication No. 24194/1980 (laid-open on Feb. 21, 1980; corresponding to West German OLS No. 2835157) discloses N-substituted alpha-halogeno-acetanilides represented by the following formula, and a process for production thereof.

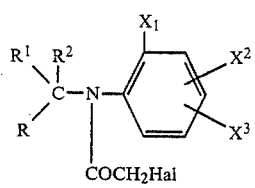

wherein

R represents an unsubstituted or substituted N-containing heterocyclic group bonded through the ring nitrogen atom, a group of the following formula

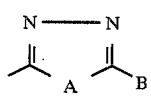

an unsubstituted or substituted furyl or thiophenyl group, an alkenyl group, an alkynyl group, an alkoxy group, an alkylcarbonyl group, or a unsubstituted or substituted phenyl, phenoxy or phenylcarbonyl group, A represents oxygen, sulfur or the group $>NR^3$, B represents hydrogen, an alkyl group, a halogenoalkyl group, an alkenyl group, an alkynyl group, a cycloalkyl group, halogen, an unsubstituted or substituted aryl or aralkyl group, the group —OR⁴, the group —SR⁴ or the group —NR³R⁴, R¹ and R², independently from each other, represent hydrogen, an alkyl group, a cycloalkyl group, a halogenoalkyl group, an alkoxyalkyl group, an alkenyl group, an alkynyl group or an unsubstituted or substituted phenyl group, R³ represents hydrogen, alkyl or substituted or unsubstituted aryl group, R⁴ represents hydrogen, an alkyl group, a halogenoalkyl group, an alkenyl group, an alkynyl gorup, a cycloalkyl group, or an unsubstituted or substituted aralkyl group, X¹, X² and X³, independently from each other, represent hydrogen or an alkyl group, and Hal represents halogen.

As is seen from the definition of R above, this Japanese patent document describes a process for producing the compounds of the above general formula which cannot include the

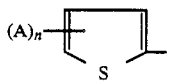

moiety specified in the compounds of this invention represented by formula (I). The Japanese patent document states that the above compounds have herbicidal and fungicidal activities, but gives no data on these activities.

Example 6 of the Japanese document describes an example of producing the following compounds which cannot be included within the above general formula given in the Japanese document.

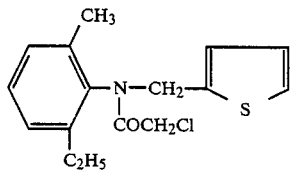

This compound cannot be included within the formula (I) in the present invention, and cannot achieve the unexpected and surprisingly excellent effects which the novel compounds of the present invention exhibit, as is shown by the results of comparative tests given in Examples 7, 8, 9 and 10.

N-substituted-chloroacetanilide herbicides which have been marketed and put to practical use, such as butachlor and alachlor, show herbicidal activity on paddy weeds at relatively low concentrations of, for example, 125 g/10a, as shown by the results of comparative tests given in Examples 7 and 8. These compounds, however, have the serious defect that at concentrations which exhibit herbicidal activity, they cause undesirable phytotoxicity to rice plants.

Herbicides which must be used in relatively high dosages to obtain significant herbicidal activity are likely to cause hazards to aquatic animals as a result of flowing into river waters and the like, and may eventually exert a deleterious effect on man and domestic animals. On the other hand, herbicides which show significant herbicidal activity in relatively low dosages but cause phytotoxicity to crops are very much restricted in their utilization. For example, it is apparent that paddy herbicides which show strong herbicidal activity at relatively low dosages but with attendant phytotoxicity to rice plants detract from the increasing of the rice harvest per unit area which is the original purpose of using the herbicides. It has been strongly desired therefore to develop a herbicide having "selective herbicidal activity" which has a herbicidal efficacy even when used in low dosages and which causes only weeds to wither.

The present inventors made extensive investigations in order to develop a compound which meets the above requirement and has excellent properties as a herbicide.

These investigations have led to the successful synthesis of N-substituted chloroacetanilides of formula (I) not described in the known literature. It has been found that unlike analogous known compounds, the compounds of formula (I) show such an unexpected and surprisingly excellent selective herbicidal efficacy that they exhibit weed controlling activity high enough to wither annual weeds including barnyard grass, a gramienous weed, and perennial weeds such as *Cyperus seroninus* Rottr. at low dosages of, for example about 15 g/10a or less and yet do not cause phytotoxicity to rise plants in high dosages of, for example, 500 g/10a.

It is an object of this invention therefore to provide the compounds of formula (I) which are useful as herbicides, particularly for paddies and which are not described in the known literature.

Another object of this invention is to provide processes for producing the compounds of formula (I), and a herbicidal composition containing such a compound of formula (I).

The above and other objects and advantages of this invention will become more apparent from the following description.

The novel compounds of this invention are expressed by the following formula (I).

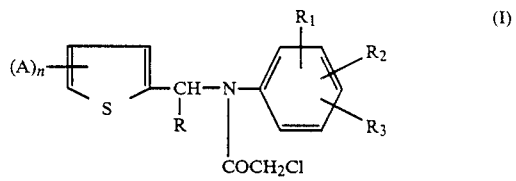

wherein

A represents a member selected from the class consisting of halogen atoms, alkoxy groups having a linear or branched, saturated or unsaturated $C_1$–$C_6$ alkyl group, alkylthio groups having a linear or branched, saturated or unsaturated $C_1$–$C_6$ alkyl group, and alkoxyalkyl groups having a linear or branched, saturated or unsaturated $C_1$–$C_6$ alkyl group and having a linear or branched, saturated or unsaturated $C_1$–$C_6$ alkylene group, $R_1$, $R_2$ and $R_3$ are identical or different, and each represents a hydrogen atom, a halogen atom, a linear or branched, saturated or unsaturated $C_1$–$C_6$ alkyl group, an alkoxy group having a linear or branched, saturated or unsaturated $C_1$–$C_6$ alkyl group, or an alkylthio group having a linear or branched saturated or unsaturated $C_1$–$C_6$ alkyl group R is a hydrogen atom or a linear or branched, saturated or unsaturated $C_1$–$C_4$ alkyl group, and n represents 1 or 2, and when n is 2, the two A's may be identical or different.

In formula (I), examples of the alkoxyalkyl group represented by A are methoxymethyl, ethoxymethyl, ethoxyethyl, propoxymethyl, propoxyethyl, butoxymethyl, butoxyethyl and butoxybutyl groups. Examples of the halogen atoms represented by A, $R_1$, $R_2$ and $R_3$ are chlorine, bromine, fluorine and iodine atoms. Examples of the alkoxy groups represented by A, $R_1$, $R_2$ and $R_3$ in formula (I) are methoxy, ethoxy, n-propoxy, t-butoxy, n-pentoxy, n-hexoxy and allyloxy groups. Examples of the alkylthio groups represented by A, $R_1$, $R_2$ and $R_3$ in formula (I) are methylthio, ethylthio, n-propylthio, t-butylthio, n-pentylthio, n-hexylthio and allylthio groups. Examples of the alkyl group represented by $R_1$, $R_2$ and $R_3$ in formula (I) are methyl, ethyl, n-propyl, iso-propyl, n-butyl, iso-butyl, t-butyl, n-pentyl, n-hexyl, allyl and ethynyl groups. The alkyl group represented by R in formula (I) may, for example, be a linear or branched, saturated or unsaturated $C_1$–$C_4$ alkyl group.

As will be clearly demonstrated in Examples given hereinbelow, the compounds of the invention represented by general formula (I) are nontoxic and safe even when applied in high concentrations of, for example, 500 g/10a, and have high enough herbicidal activity to wither completely annual weeds such as barnyard grass (*Echinochloa crus-galli*), umbrella plant (*Cyperus difformis* L.), three-square grass (*Scirpus juncoides* Roxb.) and monochoria (*Monochoria vaginalis* Presl.), and perennial weeds such as *Cyperus seroninus* Rottr., river bulrush (*Scirpus planiculmis* Fr. Schm.) and water chestnut (*Eleocharis kuroguwai* Ohwi). For example, as is clear from Examples given hereinbelow, the above compounds exhibit complete selective herbicidal activity on barnyard grass grown to a 1.5-leaf stage when applied in a dosage of as low as 30 g/10a. Furthermore, they exhibit herbicidal activity high enough to wither *Cyperus serotinus* completely in a dosage of less than 30 g/10a not only during germination but also in the growing period (height 5 to 8 cm).

This marked selective herbicidal activity, as is clear by comparison with Comparative Examples given hereinbelow, is scarcely affected by the kind of the substituent introduced into the benzene ring, but is a unique effect attributed to the halogen atom, alkoxy group, alkylthio group or alkoxyalkyl group introduced into the 3-, 4- or 5-position of the thiophene ring.

In particular, compounds of general formula (I) in which the alkoxy group is substituted at the 3-position of the thiophene ring have very strong herbicidal activity as to completely wither the aforesaid paddy weeds even at low dosages of 1.5 g/10a or below. This herbicidal activity corresponds to several times that of a conventional commercially available N-substituted-chloroacetanilide herbicide such as butachlor or alachlor.

Compounds of formula (I) which have a substituent at the 3-position of the thiophene ring and substituents at the 2- and 6-positions of the phenyl group have especially superior herbicidal effects and marked freedom from phytotoxicity on crops when used as herbicides. For example, they are N-substituted chloroacetanilides represented by the following formula (I-1) which falls within formula (I).

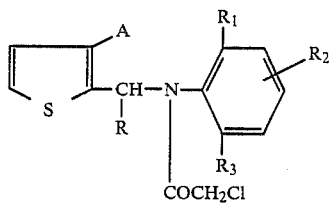

wherein A, R, $R_1$, $R_2$, $R_3$ and n are as defined above.

Preferred substituents on the thiophene ring are alkoxy groups, particularly a methoxy group, and alkoxyalkyl groups, particularly a methoxymethyl group, and next preferred are halogen atoms. Suitable substituents on the phenyl group are lower alkyl groups such as a methyl, ethyl or propyl group, alkoxy groups such as a methoxy group, and halogen atoms such as chlorine.

Next to the above preferred compounds, compounds of formula (I) which have a substituent, for example an alkoxy group such as a methoxy group, at the 4- or 5-position of the thiophene ring and substituents at the 2- and 6-positions of the phenyl group are preferred.

Compounds of general formula (I) having a halogen atom, an alkoxy group, an alkylthio group or an alkoxyalkyl group at the 4- or 5-position of the thiophene ring are especially safe on transplanted rice plants, and do not show phytotoxicity even at a dosage of 1,000 g/10a while they have high herbicidal activity.

As herbicides, the compounds of this invention exhibit a selective herbidical efficacy against weeds in paddies. This effect will be demonstrated by Examples given hereinbelow. Even when applied in large quantities, the compounds of this invention do not cause phytotoxicity to rice plants. Furthermore, even at low dosages, they can wither various weeds growing in paddies almost completely.

When, on the other hand, the compounds of this invention are used as herbicides for upland farms, they have a little bit inferior herbicidal efficacy to their selective herbicidal efficacy on paddy weeds, but cause no phytotoxicity to crops.

The structure of the compound of general formula (I) can be determined by the following means.

(A) When the infrared absorption spectrum of the compound is measured, there can be observed characteristic absorptions based on the CH bond in the vicinity of 3150–2800 cm$^{-1}$, and the carbonyl linkage of the amide group around 1680–1670 cm$^{-1}$.

(B) By measuring the mass spectrum of the compound and calculating the composition formula corresponding to the individual peaks observed (generally the value m/e obtained by dividing the ion mass m by the charge number e of the ions), the molecular weight of the compound and the manners of bonding of the molecule can be determined. When the sample used for the measurement is expressed by the following general formula

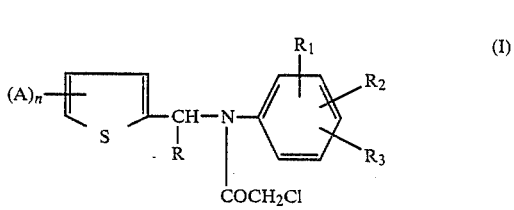

the molecular ion peak (to be abbreviated as M⊕) is generally observed in an intensity ratio corresponding to the ratio of isotopes according to the number of halogen atoms contained in the molecule. Hence, the molecular weight of the compound can be determined. Furthermore, in the compound of the invention represented by the above general formula, characteristic strong peaks corresponding to M⊕-Cl, M⊕-COCH$_2$Cl, and

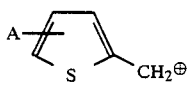

are observed, and the manners of bonding of the molecules can be determined.

(C) By measuring the $^1$H-nuclear magnetic resonance spectrum ($^1$H-nmr) of the compound, the manner of bonding of hydrogen atoms present therein can be determined. As a typical example of the $^1$H-nmr (δ, ppm: tetramethylsilane as a standard in deuterochloroform solvent) of the compound of general formula (I), the $^1$H-nmr chart of N-[2'-(5'-bromo)-thienylmethyl]-N-chloroaceto-2,6-dimethylanilide obtained in Example 4 hereinbelow is shown in FIG. 1. The results of its analysis are shown below.

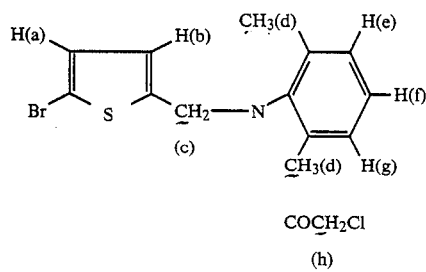

At 2.0 ppm, a singlet corresponding to 6 protons is observed and can be assigned to the methyl protons (d) substituted at the 2- and 6-positions of the phenyl group. A singlet corresponding to 2 protons is observed at 3.66 ppm and can be assigned to the methylene protons (h) in the chloroacetyl group. A singlet corresponding to 2 protons is observed at 4.75 ppm and can be assdigned to the methylene protons (c). A quartet corresponding to 2 protons is observed at 6.67 ppm and can be assigned to protons (a), (b) substituted at the thiophene ring. A multiplet corresponding to 3 protons is observed at 6.95 to 7.30 ppm and can be assigned to protons (e), (f) and (g) substituted at the phenyl group.

In summary, in the $^1$H-nmr of the compound of general formula (I), the methylene proton of the chloroacetyl group generally appears as a characteristic peak around 3.6–3.8 ppm as a singlet; the methylene protons of the aminomethylene group, around 4.8 ppm as a singlet (sometimes as a doublet when substituents exist non-symmetrically at the 2- and 6-positions of the aniline moiety); the proton of the thiophene ring, at 5.8–7.4 ppm (at the 5-position of the thiophene ring); and the protons on the benzene ring, at 6.0–7.7 ppm.

(D) The weight percents of carbon, hydrogen, nitrogen, sulfur and halogen are measured by elemental analysis. The weight percent of oxygen can be calculated by subtracting the sum of the weight percents of these elements from 100. Accordingly, the composition formula of the compound can be determined.

The N-substituted-(2-thienylmethyl)-N-chloroacetanilides of this invention slightly vary in their property depending upon the kinds of A, R, R$_1$, R$_2$ and R$_3$ in the above general formula, but are generally pale yellow or yellow viscous liquids or solids at room temperature under normal atmospheric pressure, and many of them have very high boiling points. As is the case with general organic compounds, the compounds of this invention tend to have higher boiling points as their molecular weights increase. This tendency is more specifically shown in Examples given hereinbelow. The compounds of this invention are soluble in general organic solvents such as benzene, ethers such as ethyl ether or tetrahydrofuran, alcohols such as methyl alcohol and ethyl alcohol, chloroform, carbontetarchloride, acetonitrile, N,N-dimethyl formamide and dimethyl sulfoxide, but are hardly soluble in water.

There is no particular limitation on the method of producing the compounds of this invention represented by general formula (I). Typical methods are described below, and specific examples will be given in Examples.

According to one embodiment of this invention, there can be provided a process for producing the compound of formula (I), which comprises reacting a substituted aniline represented by the following formula (II)

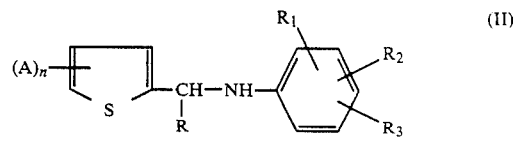

where A, R, R$_1$, R$_2$, R$_3$ and n are as defined hereinabove, with a chloroacetyl halogenide represented by the following formula (III)

wherein X represents a halogen atom.

The starting aniline derivative of general formula (II) may be one which is obtained by any methods.

In the reaction of the compound of formula (II) with the chloroacetyl halogenide of formula (III), the mole ratio of the two compounds can be determined as required. Generally, they may be used in equimolar proportions, or the chloroacetyl halogenide may be used in a slight excess.

In the above reaction, hydrogen halide is formed as a by-product. The hydrogen halide reacts with the compound of formula (II), and may cause a decrease in the yield of the final desired product. Usually, therefore, it is preferred to add a hydrogen halide capturing agent in the reaction system. The hydrogen halide capturing agent may be any known one, and examples are trialkylamines (trimethylamine, triethylamine, tripropylamine), pyridine, sodium alcoholate, and sodium carbonate.

Generally, an organic solvent is preferably used in performing the above reaction. Suitable organic solvents include, for example, aliphatic or aromatic hydrocarbons or halogenated hydrocarbons, such as benzene, toluene, xylene, hexane, heptane, petroleum ether, chloroform, methylene chloride and ethylene chloride; ethers such as diethyl ether, dioxane and tetrahydrofuran; ketones such as acetone and methyl ethyl ketone; nitriles such as acetonitrile; N,N-dialkylamides such as N,N-dimethylformamide and N,N-diehylformamide; and dimethyl sulfoxide.

The sequence of adding the starting materials in the above reaction is not particularly restricted. Generally, it is preferred to dissolve the compound of formula (II) in a solvent, charge the solution into a reactor, and then add a solvent solution of the chloroacetyl halogenide of formula (II) to it with stirring. Needless to say, the starting materials may be continuously fed to the reaction system, and the resulting product can be continuously taken out from the reaction system.

The reaction temperature may be selected within a broad range and is, for example, $-20°$ C. to $150°$ C., preferably $0°$ C. to $120°$ C. The reaction time can be properly selected depending upon the kinds of the starting materials, too. For example, it is 5 minutes to 10 days, preferably 1 to 40 hours. Preferably, the reaction is carried out with stirring.

Isolation of the final desired compound of formula (I) from the reaction mixture and its purification can be carried out by any known methods. For example, the reaction mixture is cooled or allowed to cool spontaneously to room temperature or a temperature in its vicinity, and the reaction solvent and the remaining hydrogen halide capturing agent are evaporated. The residue is extracted, for example, with benzene. By the above procedure, the salt formed from the by-product hydrogen halide and the hydrogen halide capturing agent, and high-molecular-weight compounds are separated. The benzene layer is dried over a dryer such as anhydrous sodium sulfate and calcium chloride, and benzene is evaporated. Vacuum distillation of the residue gives the final desired product. Instead of vacuum distillation, the final product may be purified by chromatography. Or when the product is a solid, it may be purified by recrystallization from a solvent such as hexane.

According to another aspect of this invention, there is provided a process for producing the compound of formula (I), which comprises reacting a 2-substituted thiophene represented by the following formula (IV)

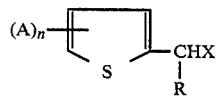

(IV)

wherein A, R and n are as defined, and X represents a halogen atom,
with a chloroacetanilide represented by the following formula (V)

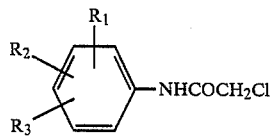

(V)

wherein $R_1$, $R_2$ and $R_3$ are as defined.

In this embodiment, the 2-substituted thiophene of formula (IV) and the chloroacetanilide of formula (V) may be those which are obtained by any desired methods. The various conditions for performing this reaction and the method of isolating and purifying the final product are substantially the same as described above with regard to the reaction of the compound of formula (II) with the chloroacetyl halogenide of formula (III).

The compounds of general formula (I) have a very superior herbicidal efficacy, for example, in the pre-emergence and post-emergence soil treatment of gramineous weeds, broad-leaved weeds and perennial weeds. They show a particularly high herbicidal efficacy on gramineous weeds, for example on barnyard grass not only during its germination but also in its 1.5-leaf stage. Yet they have high safety on rice plants not only in their 1.5-leaf stage but also during their germination. The period within which the compounds of this invention can be suitably applied is much longer than that within which conventional herbicides can be suitably applied.

They also exhibit a selective herbicidal effect when used as herbicides for upland farms. Accordingly, the compounds of this invention can be applied without injury to not only broad-leaved crops such as soybean, cotton and beet but also gramineous crops such as wheat, barley, corn and upland rice.

The present invention can therefore provide a herbicidal composition comprising a herbicidally effective amount of an N-substituted chloroacetanilide of formula (I) given hereinabove and a herbicidally acceptable diluent or carrier. The composition is particularly useful for application to paddies.

Any known herbicidally acceptable diluents or carriers can be used to prepare the herbicidal composition of this invention. They may, for example, be liquid or solid diluents or carriers.

Specific examples of liquid diluents or carriers include paraffinic or naphthenic hydrocarbons such as kerosene, mineral oil, spindle oil and white oil; aromatic hydrocarbons such as benzene, toluene, xylene, ethylbenzene, cumene and methylnaphthalene; chlorinated hydrocarbons such as carbon tetrachloride, chloroform, trichloroethylene, monochlorobenzene and o-chlorotoluene; ethers such as dioxane and tetrahydrofuran; ketones such as acetone, methyl ethyl ketone, diisobutyl ketone, cyclohexanone, acetophenone and isophorone; ester such as ethyl acetate, amyl acetate, ethylene glycol acetate, diethylene glycol acetate, dibutyl maleate and diethyl succinate; alcohols such as methanol, n-hexanol, ethylene glycol and diethylene glycol; ether alcohols such as ethylene glycol ethyl ether, ethylene glycol phenyl ether, diethylene glycol ethyl ether and diethylene glycol butyl ether; polar solvents such as dimethylformamide and dimethyl sulfoxide; and water.

Specific examples of solid diluents or carriers include clays typified by clays of the kaolinite, montmorillonite and attapulgite groups and zieclite; inorganic materials such as talc, mica, pyrophyllite, pumice, vermiculite, gypsum, calcium carbonate, dolomite, diatomaceous earth, magnesium lime, apatite, zeolite, silicic anhydride, synthetic calcium silicate; organic vegetable materials such as soybean flour, tobacco flour, chustnut flour, wheat flour, wood flour, starch and crystalline cellulose; synthetic or natural polymeric compounds such as coumarone resin, petroleum resin, alkyd resins, polyvinyl chloride, polyalkylene glycol, ketone resins, ester gum, copal gum and dammar gum; waxes such as carnauba wax and beeswax; and urea.

The content of the compound of formula (I) in the herbicidal composition can be properly selected, and may, for example, be 0.01 to 95% by weight based on the weight of the entire composition.

Some typical embodiments of using the compounds of general formula (I) as herbicides are shown below.

When the compound of general formula (I) is applied in a concentration of 1.5 g/10a to paddy soil in which seeds of barnyard grass and rice were simultaneously sown, the germination of barnyard grass can be completely inhibited. It does not cause any phtotoxicity to rice even when applied in a concentration of 1000 g/10a. Accordingly, the compound of this as a herbicide is applied to a paddy in a concentration of generally about 1.5 g to about 2,000 g/10a, preferably about 15 g to about 500 g/10a, as the amount of the active ingredient.

Since the compound of formula (I) shows selectivity in herbidical activity between barnyard grass and rice, it can be applied at a time ranging from the germinating period of rice to its growing period. Particularly, the compound of the invention has the advantage that it can be safely applied to water-seeded rice.

This invention, therefore, provides a method of controlling paddy weeds, which comprises applying the N-substituted chloroacetanilide of formula (I) to a paddy in an amount of about 1.5 to about 2,000 g per 10a of paddy.

The compounds of general formula (I) in accordance with this invention have somewhat differing herbicidal effects depending upon the differences in the kinds of functional groups, but are commonly characterized by reduced phytotoxicity to gramineous crops, particularly extremely low phytotoxicity to aquatic rice plants.

For example, the compounds of the invention have a high herbicidal efficacy againt gramineous weeds, particularly barnyard grass, and a marked herbicidal efficacy against cyperaceous weeds such as umbrella plant, *Cyperus serotinus* and three-square grass. Furthermore, they have next excellent herbicidal efficacies against broadleaved weeds. Sometimes, better results can be obtained by increasing the amount of the active ingredient or using the herbicide in combination with known herbicides such as phenoxy compounds, amide compounds, diazine compounds, carbamate compounds, urea compounds, triazine compounds, toluidine compounds, diphenylether compounds, phosphorous compounds, guaternary ammonium compounds, aliphatic compounds, benzoic acid compounds, pyridine compounds, phenol compounds, quinone compounds, nitrile compounds, pyridazine and pyridazone compounds, uracil compounds, pyrimidine compounds, imidazole compounds, acetophenone compounds, hydrazone compounds, oxime compounds or inorganic compounds. The following combinations, for example, exhibit a synergistic herbicidal efficacy.

A combination of the compound of formula (I) with an amide derivative of the following formula (a)

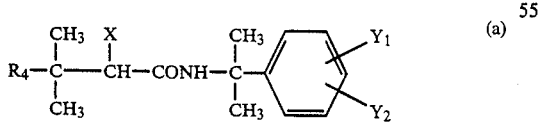

wherein $R_4$ represents an alkyl group, X represents a halogen atom, and $Y_1$ and $Y_2$ are identical or different and each represents a hydrogen atom, a halogen atom, an alkyl group or an alkoxy group.

In formula (a), examples of the alkyl group for $R_4$, $Y_1$ and $Y_2$ are alkyl groups having 1 to 4 carbon atoms, such as methyl, ethyl, n-propyl, iso-propyl, n-butyl, iso-butyl and tert-butyl groups. Examples of the alkoxy group for $Y_1$ and $Y_2$ are alkoxy groups having 1 to 4 carbon atoms, such as methoxy, ethoxy, n-propoxy, iso-propoxy, n-butyl, iso-butyl and tert-butyl groups. Examples of the halogen atom for X, $Y_1$ and $Y_2$ are fluorine, chlorine, bromine and iodine atoms.

A combination of the compound of formula (I) with a pyrazole derivative of the following formula (b)

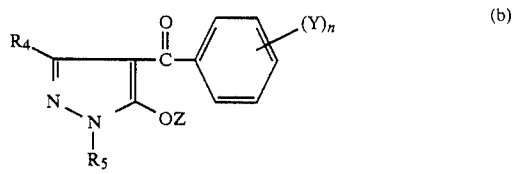

wherein $R_4$ and $R_5$ represent an alkyl group, Y represents a halogen atom or a nitro group, n is 1 or 2, and Z represents an alkyl group, an acetylalkyl group, a substituted or unsubstituted phenyl group, a benzyl group, a phenacyl group, or a group of the formula

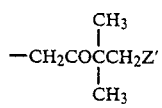

in which Z' represents a hydrogen or halogen atom. In the formula (b), examples of the alkyl group for $R_4$ and $R_5$ are alkyl groups having 1 to 3 carbon atoms, such as methyl, ethyl, n-propyl and iso-propyl groups. Examples of the alkyl group for Z are alkyl groups having 1 to 3 carbon atoms such as methyl, ethyl, n-propyl and iso-propyl groups. Examples of the acetylalkyl group for Z are acetylalkyl groups having a $C_1$-$C_3$ alkyl group, such as acetylmethyl, acetylethyl, acetyl-n-propyl and acetyl-iso-propyl groups. Examples of the substituted phenyl group for Z are substituted phenyl groups having such a substituent as fluoro, chloro, bromo, iodo, nitro, methyl, ethyl, n-propyl, iso-propyl, methoxy, ethoxy, n-propoxy, or iso-propoxy. Examples of the halogen atom for Y and Z' are fluorine, chlorine, bromine and iodine atoms.

A combination of the compound of formula (I) with an alpha-(beta-naphthoxy)-propionic acid derivative represented by the following formula (c)

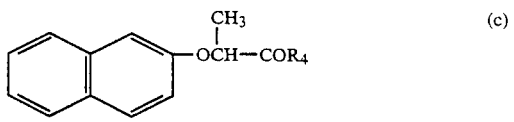

wherein $R_4$ represents —$OR_5$ or

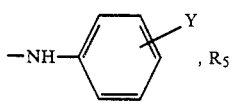

represents an alkyl group and Y represents a hydrogen or a halogen atom, and a thiocarbamate derivative represented by the following formula (d)

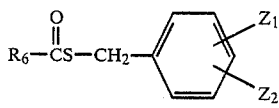
(d)

wherein $R_6$ is

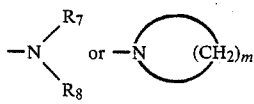

in which $R_7$ and $R_8$ represent a hydrogen atom or an alkyl group, and m is an integer of 3 to 8;

and $Z_1$ and $Z_2$ are identical or different and each represents a hydrogen atom, a halogen atom, an alkyl group or an alkoxy group.

In formula (c), examples of the alkyl group for $R_5$ are alkyl groups having 1 to 4 carbon atoms such as methyl, ethyl, n-propyl, iso-propyl, n-butyl, iso-butyl and tert-butyl groups. Examples of the halogen atom for Y are fluorine, chlorine, bromine, and iodine atoms.

In formula (d), examples of the alkyl group for $R_7$ and $R_8$ are alkyl groups having 1 to 4 carbon atoms, such as methyl, ethyl, n-propyl, iso-propyl, n-butyl, iso-butyl and tert-butyl groups. Examples of the halogen atom for $Z_1$ and $Z_2$ are fluorine, chlorine, bromine and iodine atoms. Examples of the alkyl group for $Z_1$ and $Z_2$ are alkyl groups having 1 to 4 carbon atoms, such as methyl, ethyl, n-propyl, iso-propyl, n-butyl, iso-butyl and tert-butyl groups. Example of the alkoxy group for $Z_1$ and $Z_2$ are alkoxy groups having 1 to 4 carbon atoms such as methoxy, ethoxy, n-propoxy, iso-propoxy, n-butoxy, iso-butoxy and tert-butoxy groups.

A combination of the compound of formula (I) with an alpha-(beta-naphthoxy)propionic acid derivative of the following formula (e)

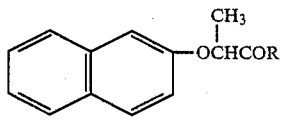
(e)

wherein R represents —OCH$_3$,

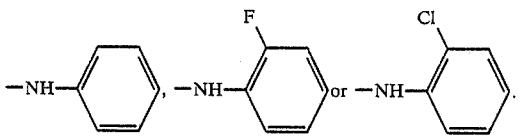

Examples of weeds which can be effectively controlled by using the herbicide of this invention comprising the compound of formula (I) as an active ingredient.

Paddy weeds
  Barnyard grass (*Echinochloa crus-galli* Beauv.; *Echinochloa oryzicola* Vasing),
  Beckmann's grass (*Beckmannia syzigachne* (Steud.) Fernald),
  umbrella plant (*Cyperus difformis* L.),
  "mizuhanabi" (*Cyperus tenuispica* Steud.),
  "hinagayatsuri" (*Cyperus flaccidus* R. Br.),
  "kawarasugana" (*Cyperus sanguinolenlus* Vahl.),
  three-square grass (*Scirpus juncoides* Rxb.),
  spikerush (*Eleocharis congesta* D. Dun.),
  fimbristylis (*Fimbristylis dicholoma* Vahl),
  fimbristylis (*Fimbristylis autumnalis* Roem. et Schult.),
  "hideriko" (*Fimbristylis miliacea* Vahl.),
  "mizugayatsuri" (*Cyperus serotinus* Rottr.),
  "himekugu" (*Kyllinga brevifolia* Rottr.),
  water chustnut (*Eleocharis kuroguwai* Ohwi),
  slender spikerush (*Eleocharis acicularis* Roem. et Schult.,
  river bulrush (*Scirpus planiculmis* Fr. Schm.),
  arrowhead (*Sagittaria trifolia* L.),
  "aginashi" (*Sagittaria aginashi* Makino),
  narrowleaf waterplaintain (*Alisma canaliculatum* A. Bn. et Bouche),
  "urikawa" (*Sagittaria pyqmaea* Miq.),
  largeleaf pondweed (*Potamogelon distinctus* A. Benn.),
  pepperwort (*Marsilea quadrifolia* L.),
  dropwort (*Oenanthe javanica* de Candolle),
  water pepper (*Polygonum hydropiper* L.),
  monochoria (*Monochoria vaginalis* Presl.),
  "ibokusa" (*Aneilema keisak* Hand-Mazt.),
  pipewort (*Eriocauton sieboldianum* Sieb. et Zucc.),
  water wort (*Elatine triandra* Schk.),
  "himemisohagi" (*Ammannia multiflora* Roxb.),
  "kikashigusa" (*Rotala indica* Koehne.),
  "mizumatsuba" (*Rotala mexicana* Cham. et Schletdl.),
  false loostrife (*Lugwigia prostrata* Roxb.),
  "azemushiro" (*Lobelia chinensis* Lour.),
  American false daisy (*Eclipta prostrata* L.),
  burmarigold (*Bidens tripartita* L.),
  devil's beggarticks (*Bidens frondosa* L.),
  "akanumaso" (*Gratiola violacea* Maxim.),
  "sawatogarashi" (*Deinostema violacea* Yamazaki),
  "abunome" (*Dopatrium junceum* Hamilt.),
  false pimpernel (*Lindernia pyxidaria* L.), and
  "azetogarashi" (*Vandellia angustifolia* Bentham).

Upland farm weeds
  Large crabgrass (*Digitaria ciliaris* Koeler),
  green foxtail (*Setaria viridis* Beauv.),
  common lambsquaters (*Chenopodium album* L.),
  smartweed (*Polygonum longisetum* De. Bruyn.),
  yellow nutsedge (*Cyperus microiria* Steud.),
  yellow cyperus (*Cyperus iria* L.),
  pigweed (*Amaranthus lividus* L.),
  common purslane (*Portulaca oleracea* L.),
  red clover (*Trifolium pratense* L.),
  creeping woodsorrel (*Oxalis corniculata* L.),
  water foxtail (*Alopecurus aequalis* Sorol.),
  annual bluegrass (*Poa annua* L.),
  bedstraw (*Galium spurium* L.),
  blue morning glory (*Ipomoea indica* Merrill),
  "kawaraketsumei" (*Cassia nomame* Honda),
  common vetch (*Vicia sativa* L.), and
  shepherd's purse (*Capsella bursa-pastoris* Medik.).

The compounds of this invention represented by formula (I) can also be used as defoliants, germination inhibitors and growth regulators because they affect the growth of plants.

The form in which the compounds of formula (I) are used is not particularly restricted, and they can be used in any known forms of herbicides. For example, they can be formulated into granules, dusts, emulsifiable concentrates, wettable powders, tablets, oil solutions, aerosols, fumigants, etc. Adjuvants such as spreaders, diluents, surface-active agents and solvents may be incorporated as required for formulation purposes.

The compounds of general formula (I) can also be used as a mixture with insecticides, fungicides, other agricultural chemicals, fertilizers, and soil conditioners.

The following examples illustrate the present invention. It should be understood that the invention is not limited to these specific examples.

EXAMPLE 1

Figure 2:
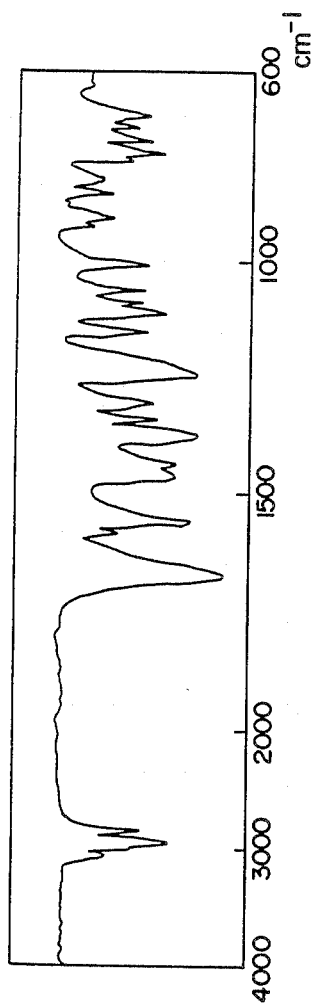

5.81 g (0.024 mole) of N-[2'-(3'-methoxy)-thienylmethyl]-2,6-dimethylaniline was dissolved in 40 ml of benzene, and 3.10 g (0.031 mole) of triethylamine was added. The solution was placed in ice water. Then, a benzene solution (15 ml) of 3.19 g (0.028 mole) of chloroacetyl chloride was gradually added. The mixture was stirred for 3 hours, and then heated at 50° C. for 3 hours. The reaction mixture was cooled to room temperature and then washed successively with 50 ml of water, 50 ml of 2N-HCl and then 50 ml of water. The benzene layer was dried over anhydrous sodium sulfate. Benzene was evaporated under reduced pressure, and the residue was vacuum-distilled to give 5.03 g of a pale yellow solid having a boiling point of 172° C./0.15 mmHg. The infrared spectrum of this product was measured, and is shown in FIG. 2. The infrared spectrum showed an absorption based on the C—H bond at 3100–2800 cm$^{-1}$ and a strong absorption on the carbonyl linkage of the amide group at 1670 cm$^{-1}$.

The elemental analysis values were C59.20%, H5.64%, N4.37% which well agreed with the calculated values for the composition formula $C_{16}H_{18}NSO_2Cl$ (323.84), i.e. C59.33%, H5.61%, N4.33%.

The mass spectrum of the product showed a molecular ion peak M⊕ corresponding to its molecular weight at m/e 323, a peak corresponding to M⊕-Cl at m/e 288, a peak corresponding to M⊕-COCH$_2$Cl at m/e 246, and a peak corresponding to

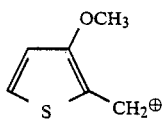

at m/e 127 (100%).

Figure 3:
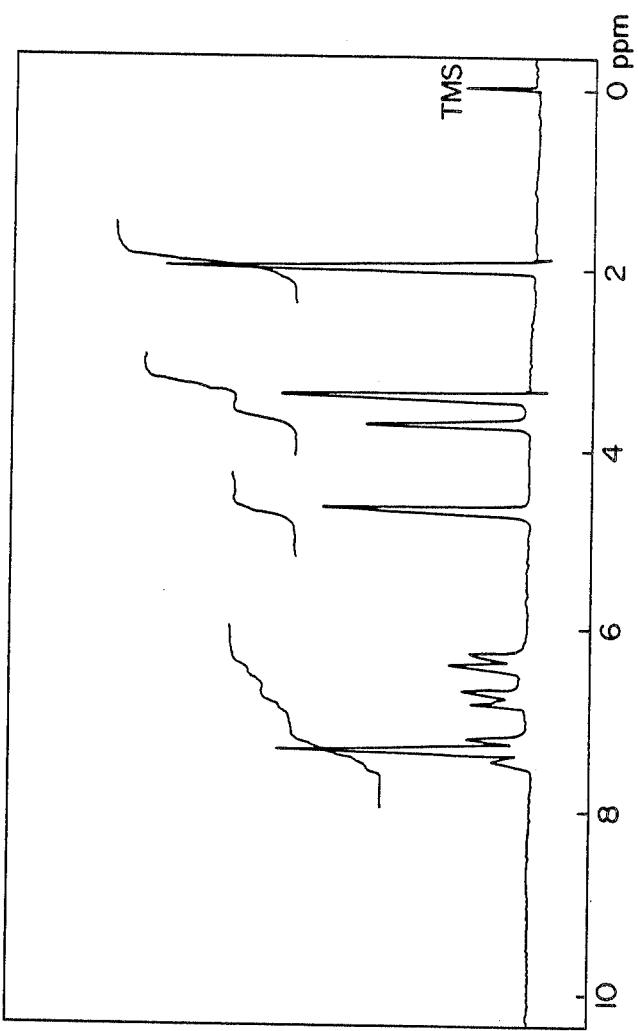

The results of measuring the $^1$H-nmr spectrum (δppm; tetramethylsilane as a standard in deuterochloroform as a solvent) of the product are shown in FIG. 3. The results of its analysis were as follows:

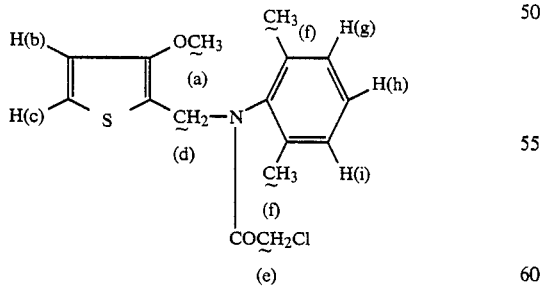

A singlet corresponding to 6 protons exists at 1.95 ppm and is assigned to the methyl protons (f) substituted at the 2- and 6-positions of the phenyl group. A singlet corresponding to 3 protons exists at 3.50 ppm and is assigned to the methyl protons (a). A singlet corresponding to 2 protons exists at 3.72 ppm and is assigned to the methylene protons (e). A singlet corresponding to 2 protons exists at 4.75 ppm and is assigned to the methylene protons (d). Two doublets corresponding to 2 protons exist at 6.55 ppm and are assigned to the protons (b) and (c) of the thiophene ring. A multiplet corresponding to 3 protons exists at 7.00–7.45 ppm and is assigned to the protons (g), (h) and (i) of the benzene ring.

The foregoing results led to the determination that the isolated product was N-[2'-(3'-methoxy)-thienylmethyl]-N-chloroaceto-2,6-dimethylanilide. The yield was 66.2% (0.016 mole) based on N-[2'-(3'-methoxy)-thienylmethyl]-2,6-dimethylaniline.

EXAMPLE 2

2.71 g (0.012 mole) of 2,6-diethyl-N-chloroacetanilide, 2.12 g (0.012 mole) of 2-chloromethyl-5-ethoxythiophene and 0.83 g (6.0×10$^{-3}$ mole) of potassium carbonate were added to 50 ml of N,N-dimethylformamide (to be abbreviated as DMF), and the mixture was stirred. The reaction mixture was heated at 100° C. for 3 hours, and then stirred at room temperature for 1 hour. The precipitated potassium chloride was separated by filtration, and DMF in the filtrate was evaporated under reduced pressure. Water (100 ml) was added to the residue, and the mixture was extracted with ether. The ethereal layer was dried over anhydrous sodium sulfate, and ether was evaporated under reduced pressure. The residue was vacuum-distilled to give 3.50 g of a yellow viscous liquid having a boiling point of 182° C./0.30 mmHg.

The infrared spectrum of this product measured showed an absorption based on the C—H bond at 3100–2800 cm$^{-1}$ and a strong absorption based on the carbonyl linkage of the amide group at 1670 cm$^{-1}$.

The mass spectrum of the product measured showed a molecular ion peak M⊕ corresponding to the molecular weight of the product at m/e 365, a peak corresponding to M⊕-Cl at m/e 330, a peak corresponding to M⊕-COCH$_2$Cl at m/e 288, and a peak corresponding to

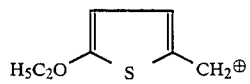

at m/e 141 (100%).

Figure 4:
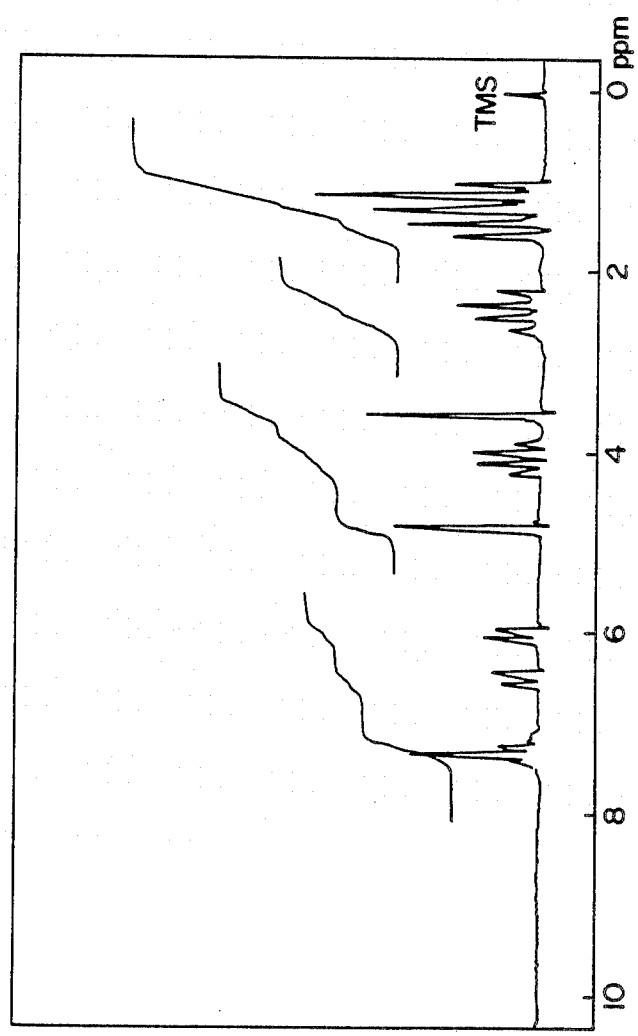

The $^1$H-nmr spectrum (δppm; tetramethylsilane as a standard in deuterochloroform as a solvent) of the product measured is shown in FIG. 4. The results of its analysis were as follows:

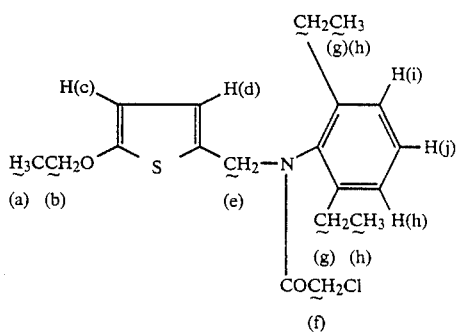

A triplet corresponding to 6 protons exists at 1.15 ppm, and is assigned to the methyl protons (h) of the ethyl groups substituted at the 2- and 6-positions of the phenyl group. A triplet corresponding to 3 protons exists at 1.40 ppm and is assigned to the methyl proton (a) of ethoxy group substituted at the thiophene ring. A quartet corresponding to 4 protons exists at 2.39 ppm, and is assigned to the methylene protons (g) of the ethyl groups substituted at the 2- and 6-positions of the phenyl groups. A singlet corresponding to 2 protons exists at 3.66 ppm and is assigned to the methylene proton (f). A quartet corresponding to 2 protons exists at 4.04 ppm and is assigned to the methylene protons (b) of the ethoxy group substituted on the thiophene ring. A singlet corresponding to 2 protons exists at 4.75 ppm, and is assigned to the methylene protons (e) adjacent to the thiophene ring. A doublet corresponding to 1 proton exists at 5.95 ppm and is assigned to the proton (c) on the thiophene ring. A doublet corresponding to 1 proton exists at 6.39 ppm and is assigned to the proton (d) on the thiophene ring. A multiplet exists at 7.10-7.40 ppm and is assigned to the protons (i), (j) and (h) on the benzene ring.

The above results led to the determination that the isolated product was N-[2'-(5'-ethoxy)-thienylmethyl]-N-chloroaceto-2,6-diethylanilide. The yield was 79.7% ($9.57 \times 10^{-3}$ mole) based on 2,6-diethyl-N-chloroacetanilide.

EXAMPLE 3

The same reaction and work-up as in Example 1 were carried out except that 2.14 g ($7.66 \times 10^{-3}$ mole) of N-[2'-(3'-chloro)-thienylmethyl]-2-methyl-6-isopropylaniline was used instead of N-[2'-(3'-methoxy)-thienylmethyl]-2,6-dimethylaniline. There was obtained 1.08 g of a pale yellow solid having a boiling point of 167° C.

The infrared spectrum of this product measured showed an absorption based on the C—H bond at 3120-2900 cm$^{-1}$ and a strong absorption based on the carbonyl linkage of the amide group at 1675 cm$^{-1}$.

The elemental analysis values of the product were C57.47%, H5.47%, N4.03%, which agreed well with the calculated values for the composition formula $C_{17}H_{19}NSOCl_2$ (356.31), i.e. C57.30%, H5.39%, N3.93%.

The mass spectrum of the product measured showed a molecular ion peak M$^\oplus$ corresponding to its molecular weight at m/e 355, a peak corresponding to M$^\oplus$-Cl at m/e 320, a peak corresponding to M$^\oplus$-COCH$_2$Cl at m/e 277, and a peak corresponding to

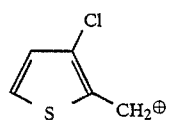

at m/e 131.

Figure 5:
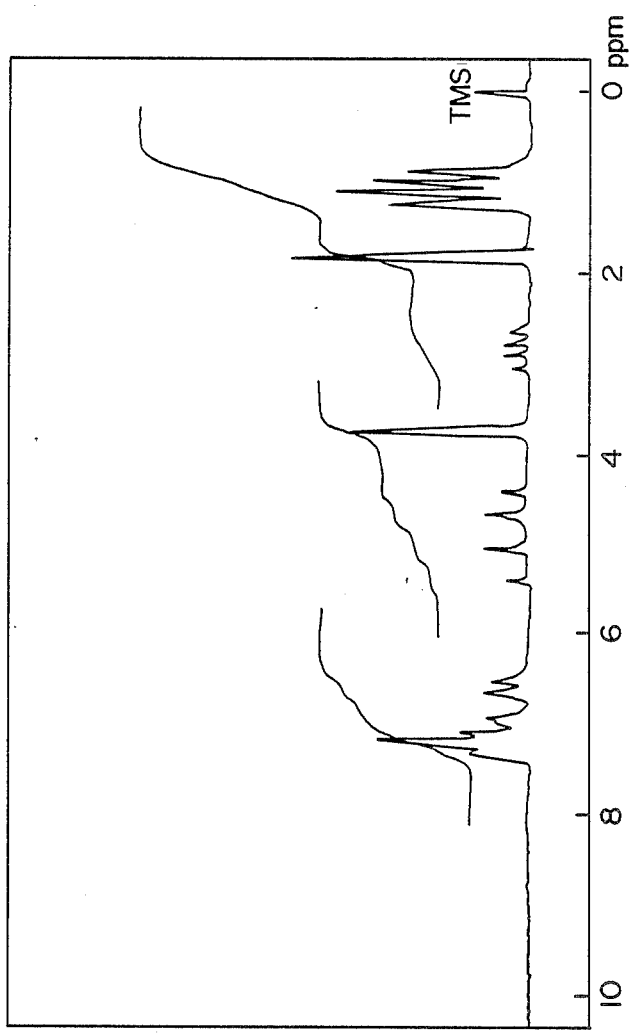

The $^1$H-nmr spectrum (δppm; tetramethylsilane as a standard in deuterochloroform as a solvent) of the product was measured and is shown in FIG. 5. The results of its analysis were as follows:

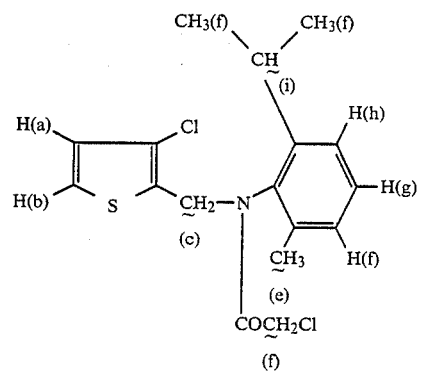

A quartet corresponding to 6 protons exists at 1.13 ppm and is assigned to the methyl protons of the two isopropyl groups substituted at the 2-position of the phenyl group. A singlet corresponding to 3 protons exists at 1.92 ppm and is assigned to the methyl protons (e) substituted at the 6-position of the phenyl group. A multiplet corresponding to 1 proton exists at 2.80 ppm and is assigned to the methine proton (i) of the isopropyl group. A singlet corresponding to 2 protons exists at 3.74 ppm and is assigned to the methylene protons (d). A quartet (geminal constant=16 Hz) corresponding to 2 protons exists at 4.93 ppm and is assigned to the methylene protons (c) adjacent to the thiophene ring. A multiplet corresponding to 2 protons exists at 6.66-7.10 ppm and is assigned to 2 protons (a) and (b) of the thiophene ring. A multiplet corresponding to 3 protons exists at 7.10-7.35 ppm and is assigned to the three protons (f), (g) and (h) of the phenyl group.

The foregoing results led to the determination that the isolated product was N-[2'-(3'-chloro)-thienylmethyl]-N-chloroaceto-2-methyl-6-isopropylanilide iropsopylanilide. The yield of the product was 39.6% ($3.03 \times 10^{-3}$ mole) based on N-[2'-(3'-chloro)-thienylmethyl]-2-methyl-6-isopropylaniline.

EXAMPLE 4

The same reaction and work-up as in Example 1 were carried out except that 1.81 g ($6.14 \times 10^{-3}$ mole) of N-[2'-(5'-bromo)-thienylmethyl-2,6-dimethylaniline was used instead of N-[2'-(3'-methoxy)-thienylmethyl]-2,6-dimethylaniline. On purification by column chromatography, 1.13 g of a yellow solid was obtained.

The infrared spectrum of the product measured showed an absorpttion based on the C—H bond at 3110-2900 cm$^{-1}$ and a strong absorption based on the carbonyl linkage of the amide group at 1670 cm$^{-1}$.

The elemental analysis values of the product were C48.43%, H4.05%, N3.99% which well agreed with the calculated values for $C_{15}H_{15}NSOBrCl$ (372.71), i.e. C48.20%, H4.32%, N3.75%.

The mass spectrum of the product measured showed a molecular ion peak M$^\oplus$ corresponding to its molecular weight at m/e 371, a peak corresponding to M$^\oplus$-Cl at m/e 336, a peak corresponding to M$^\oplus$-COCH$_2$Cl at m/e 293, and a peak corresponding

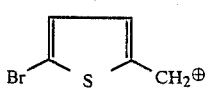

at m/e 143 (100%).

The $^1$H-nmr spectrum of the product was the same as that specifically shown hereinabove in the specification.

The foregoing results led to the determination that the isolated product was N-[2'-(5'-bromo)-thienylmethyl]-N-chloroaceto-2,6-dimethylanilide. The yield of the product was 49.5% (3.04×10$^{-3}$ mole) based on N-[2'-(5'-bromo)-thienylmethyl]-2,6-dimethylaniline.

EXAMPLE 5

By the same method as described in Examples 1 to 4, the N-substituted-chloroacetanilides shown in Table 1 were synthesized. Table 1 summarizes the forms, boiling points, characteristic IR absorption values and elemental analysis values (the values at the top were those found and the values at the bottom were those calculated) of the synthesized N-substituted-chloroacetanilide compounds.

TABLE 1

$$D-CH_2-N(COCH_2Cl)-B$$

| No. | D | B | Form | Property (b.p.) | ir (cm$^{-1}$) (C=O) | C | H | N |
|-----|---|---|------|-----------------|------------------------|-----|-----|-----|
| 1 | H$_3$CO-thienyl | phenyl | pale yellow viscous liquid | 168° C./ 0.40 mmHg | 1670 | 56.79 / 56.84 | 4.79 / 4.78 | 4.64 / 4.74 |
| 2 | H$_3$CO-thienyl | CH$_3$-phenyl | pale yellow viscous liquid | 171° C./ 0.38 mmHg | 1670 | 57.71 / 58.14 | 5.12 / 5.22 | 4.44 / 4.52 |
| 3 | H$_3$CO-thienyl | C$_2$H$_5$-phenyl | Yellow solid | 185° C./ 0.38 mmHg | 1675 | 59.30 / 59.33 | 5.65 / 5.61 | 4.57 / 4.33 |
| 4 | H$_3$CO-thienyl | 4-OC$_2$H$_5$-phenyl | Yellow viscous liquid | purified by column chromatography | 1680 | 57.01 / 56.54 | 5.38 / 5.35 | 3.98 / 4.12 |
| 5 | H$_3$CO-thienyl | 2-Cl-phenyl | yellow solid | 145° C./ 0.30 mmHg | 1680 | 50.89 / 50.91 | 3.96 / 3.98 | 4.30 / 4.24 |
| 6 | H$_3$CO-thienyl | 2-Br-phenyl | yellow solid | purified by column chromatography | 1675 | 44.25 / 44.87 | 3.58 / 3.50 | 3.74 / 3.74 |
| 7 | H$_3$CO-thienyl | 2,6-(CH$_3$)$_2$-phenyl | yellow solid | 165° C./ 0.30 mmHg | 1675 | 59.20 / 59.33 | 5.64 / 5.61 | 4.37 / 4.33 |
| 8 | H$_3$CO-thienyl | 2-CH$_3$-4-C$_2$H$_5$-phenyl | pale yellow viscous liquid | 186° C./ 0.70 mmHg | 1670 | 60.23 / 60.43 | 5.97 / 5.98 | 4.31 / 4.15 |

TABLE 1-continued $$\text{D—CH}_2\text{—N(COCH}_2\text{Cl)—B}$$

| No. | D | B | Form | Property (b.p.) | ir (cm$^{-1}$) (C=O) | Elemental analysis values (%) C | H | N |
|---|---|---|---|---|---|---|---|---|
| 9 | 5-methoxy-2-thienyl (H$_3$CO—[thiophene]—) | 2,6-diethylphenyl (C$_2$H$_5$, C$_2$H$_5$) | yellow solid | 175° C./ 0.30 mmHg | 1670 | 61.92 / 61.43 | 6.42 / 6.31 | 4.18 / 3.98 |
| 10 | 5-methoxy-2-thienyl | 2,4,6-trimethylphenyl (CH$_3$, CH$_3$, CH$_3$) | yellow solid | 182° C./ 0.25 mmHg | 1670 | 59.88 / 60.43 | 5.88 / 5.98 | 4.00 / 4.15 |
| 11 | 5-methoxy-2-thienyl | 2-methyl-6-isopropylphenyl (CH$_3$, (CH$_3$)$_2$CH) | pale yellow viscous liquid | 176° C./ 0.20 mmHg | 1675 | 61.45 / 61.43 | 6.32 / 6.31 | 4.08 / 3.98 |
| 12 | 5-methoxy-2-thienyl | 2-ethyl-6-isopropylphenyl (C$_2$H$_5$, (CH$_3$)$_2$CH) | yellow solid | 178° C./ 0.30 mmHg | 1680 | 61.69 / 62.36 | 6.62 / 6.62 | 3.91 / 3.83 |
| 13 | 5-methoxy-2-thienyl | 2-methyl-4-methoxyphenyl (CH$_3$, CH$_3$O) | yellow viscous liquid | 178° C./ 0.40 mmHg | 1670 | 59.30 / 59.33 | 5.65 / 5.61 | 4.57 / 4.33 |
| 14 | 5-ethoxy-2-thienyl (H$_5$C$_2$O—[thiophene]—) | 2,6-difluorophenyl (F, F) | yellow solid | 165° C./ 0.40 mmHg | 1675 | 52.08 / 52.10 | 4.07 / 4.09 | 4.06 / 4.05 |
| 15 | 5-(methoxymethyl)-2-thienyl (CH$_3$OCH$_2$—[thiophene]—) | 2,6-dimethylphenyl (CH$_3$, CH$_3$) | pale yellow viscous liquid | 175° C./ 0.15 mmHg | 1670 | 60.41 / 60.42 | 6.01 / 5.98 | 4.10 / 4.15 |
| 16 | 3-(methoxymethyl)-2-thienyl (CH$_2$OCH$_3$ on thiophene) | 2,6-dimethylphenyl (CH$_3$, CH$_3$) | white solid | 172° C./ 0.30 mmHg | 1670 | 60.36 / 60.42 | 5.83 / 5.98 | 4.00 / 4.15 |

TABLE 1-continued

D—CH₂—N—B
            |
            COCH₂Cl

| No. | D | B | Form | Property (b.p.) | ir (cm$^{-1}$) (C=O) | Elemental analysis values (%) C | H | N |
|-----|---|---|------|-----------------|----------------------|---|---|---|
| 17 | 3-OCH₃, 2-CH₃ thiophene | 2-CH₃, 6-C₂H₅ phenyl | pale yellow viscous liquid | 174° C./ 0.25 mmHg | 1670 | 61.90 / 60.43 | 6.04 / 5.98 | 4.09 / 4.15 |
| 18 | 3-OCH₃, 2-CH₃ thiophene | 2,6-(C₂H₅)₂ phenyl | yellow viscous solid | 180° C./ 0.25 mmHg | 1680 | 61.26 / 61.43 | 6.32 / 6.31 | 3.90 / 3.98 |
| 19 | 3-OCH₃, 2-CH₃ thiophene | 2-Cl, 6-CH₃ phenyl | pale yellow solid | 165° C./ 0.10 mmHg | 1670 | 52.92 / 52.33 | 4.40 / 4.40 | 4.25 / 4.04 |
| 20 | 3-OCH₃, 2-CH₃ thiophene | 2-CH₃, 6-(CH₃)₂CH phenyl | yellow viscous liquid | 175° C./ 0.35 mmHg | 1680 | 62.01 / 61.43 | 6.47 / 6.31 | 3.99 / 3.98 |
| 21 | 3-OCH₃, 2-CH₃ thiophene | 2-C₂H₅, 6-(CH₃)₂CH phenyl | pale yellow viscous liquid | 178° C./ 0.40 mmHg | 1680 | 61.61 / 62.36 | 6.62 / 6.62 | 3.91 / 3.83 |
| 22 | 3-OCH₃, 2-CH₃ thiophene | 2,5-(CH₃)₂ phenyl | pale yellow solid | 178° C./ 0.3 mmHg | 1650 | 55.10 / 55.05 | 4.35 / 4.32 | 4.26 / 4.28 |
| 23 | 3-OCH₃, 2-CH₃ thiophene | 2-OCH₃, 6-CH₃ phenyl | pale yellow solid | 183° C./ 0.35 mmHg | 1650 | 52.30 / 52.25 | 4.60 / 4.65 | 3.63 / 3.59 |
| 24 | 3-OCH₃, 5-CH₃ thiophene | 2-OCH(CH₃)₂, 6-CH₃ phenyl | pale yellow solid | purified by column chromatography | 1675 | 58.81 / 58.76 | 6.01 / 6.04 | 3.77 / 3.81 |

TABLE 1-continued $$\begin{array}{c} D-CH_2-N-B \\ | \\ COCH_2Cl \end{array}$$

| No. | D | B | Form | Property (b.p.) | ir (cm$^{-1}$) (C=O) | Elemental analysis values (%) C / H / N |
|---|---|---|---|---|---|---|
| 25 | 5-OC(CH$_3$)$_3$-thiophen-2-yl | 2-(CH$_2$)$_3$CH$_3$-phenyl | pale yellow solid | purified by column chromatography | 1670 | 63.96 7.11 3.60 / 64.01 7.18 3.56 |
| 26 | 5-O-(CH$_3$)$_2$CH$_3$-thiophen-2-yl | 4-(CH$_2$)$_5$CH$_3$-phenyl | pale yellow solid | purified by column chromatography | 1670 | 64.72 7.43 3.46 / 64.75 7.43 3.43 |
| 27 | 5-CH$_2$=CHCH$_2$O-thiophen-2-yl | 2-C(CH$_3$)$_3$-phenyl | yellow solid | purified by column | 1670 | 63.58 6.41 3.73 / 63.56 6.40 3.71 |
| 28 | 5-H$_3$CS-thiophen-2-yl | 2,6-di-CH$_3$-phenyl | yellow solid | 202° C./0.45 mmHg | 1680 | 55.36 5.29 4.09 / 56.53 5.33 4.12 |
| 29 | 5-H$_3$CS-thiophen-2-yl | 2,6-di-C$_2$H$_5$-phenyl | yellow solid | 195° C./0.09 mmHg | 1680 | 58.81 6.06 3.85 / 58.75 6.04 3.81 |
| 30 | 3-SCH$_3$-thiophen-2-yl | 2,6-di-CH$_3$-phenyl | yellow solid | 181° C./0.15 mmHg | 1670 | 56.58 5.36 4.11 / 56.63 5.35 4.12 |
| 31 | 3-SCH$_3$-thiophen-2-yl | 2-CH$_3$-6-C$_2$H$_5$-phenyl | pale yellow viscous liquid | 186° C./0.70 mmHg | 1700 | 57.51 5.92 3.96 / 57.52 5.98 3.95 |
| 32 | 3-SCH$_3$-thiophen-2-yl | 2,6-di-C$_2$H$_5$-phenyl | pale yellow solid | 182° C./0.40 mmHg | 1670 | 58.69 6.10 3.90 / 58.75 6.04 3.81 |
| 33 | 3-SC$_2$H$_5$-thiophen-2-yl | 2,6-di-CH$_3$-phenyl | pale yellow viscous liquid | 165° C./0.15 mmHg | 1680 | 57.66 5.69 3.92 / 57.68 5.71 3.96 |

TABLE 1-continued $$D-CH_2-N(COCH_2Cl)-B$$

| No. | D | B | Form | Property (b.p.) | ir (cm$^{-1}$) (C=O) | Elemental analysis values (%) C | H | N |
|---|---|---|---|---|---|---|---|---|
| 34 | 5-Br-thiophen-2-yl | 2,6-diethylphenyl | yellow solid | 178° C./ 0.30 mmHg | 1675 | 50.97 50.94 | 4.78 4.79 | 3.36 3.50 |
| 35 | 5-Br-thiophen-2-yl | 2-methyl-6-chlorophenyl | yellow solid | 185° C./ 0.30 mmHg | 1675 | 42.80 42.77 | 3.09 3.08 | 3.61 3.56 |
| 36 | 5-Br-thiophen-2-yl | 2-methyl-6-methoxyphenyl | pale yellow viscous liquid | 170° C./ 0.20 mmHg | 1670 | 47.36 46.34 | 4.08 3.90 | 3.66 3.60 |
| 37 | 4-Br-thiophen-2-yl | 2,6-dimethylphenyl | pale yellow solid | purified by column chromatography | 1675 | 48.19 48.20 | 4.31 4.32 | 3.76 3.75 |
| 38 | 4-Br-thiophen-2-yl | 2-methyl-6-methoxyphenyl | pale yellow solid | purified by column chromatography | 1680 | 46.35 46.34 | 3.92 3.90 | 3.63 3.60 |
| 39 | 5-Cl-thiophen-2-yl | 2,6-dimethylphenyl | yellow solid | 175° C./ 0.20 mmHg | 1680 | 54.91 54.88 | 4.71 4.62 | 4.31 4.27 |
| 40 | 5-Cl-thiophen-2-yl | 2,6-diethylphenyl | yellow solid | 180° C./ 0.40 mmHg | 1680 | 57.62 57.30 | 5.41 5.39 | 4.04 3.93 |
| 41 | 5-Cl-thiophen-2-yl | 2-methyl-6-methoxyphenyl | pale yellow viscous liquid | 188° C./ 0.35 mmHg | 1675 | 52.44 52.33 | 4.37 4.40 | 4.01 4.07 |

TABLE 1-continued $$\underset{\underset{COCH_2Cl}{|}}{D-CH_2-N-B}$$

| No. | D | B | Form | Property (b.p.) | ir (cm$^{-1}$) (C=O) | Elemental analysis values (%) C H N |
|---|---|---|---|---|---|---|
| 42 | 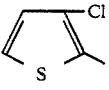 | 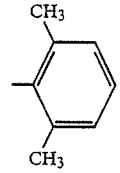 | pale yellow viscous liquid | 162° C./ 0.15 mmHg | 1670 | 55.08  4.60  4.44<br>54.88  4.62  4.27 |
| 43 | 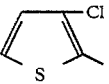 | 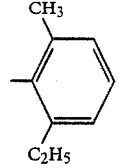 | pale yellow viscous liquid | 158° C./ 0.25 mmHg | 1680 | 56.84  5.16  4.32<br>56.14  5.02  4.09 |
| 44 | 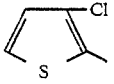 | 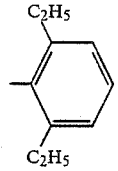 | pale yellow solid | 165° C./ 0.15 mmHg | 1670 | 57.48  5.33  3.98<br>57.30  5.39  3.93 |
| 45 | 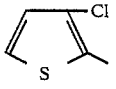 | 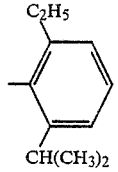 | pale yellow solid | 176° C./ 0.25 mmHg | 1670 | 58.33  5.69  3.81<br>58.37  5.73  3.78 |
| 46 | 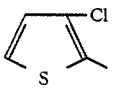 | 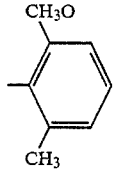 | pale yellow viscous liquid | 168° C./ 0.25 mmHg | 1670 | 53.10  4.42  4.13<br>52.33  4.40  4.07 |
| 47 | 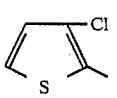 | 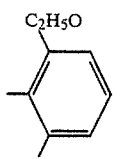 | pale yellow solid | 187° C./ 0.15 mmHg | 1670 | 53.54  4.80  3.92<br>53.63  4.79  3.91 |
| 48 | 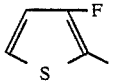 | 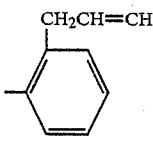 | pale yellow solid | purified by column chromatography | 1675 | 59.28  4.59  4.31<br>59.34  4.68  4.33 |
| 49 | 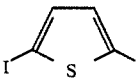 | 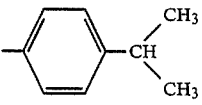 | pale yellow solid | purified by column chromatography | 1680 | 44.33  3.98  3.21<br>44.30  3.96  3.23 |
| 50 | 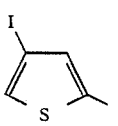 | 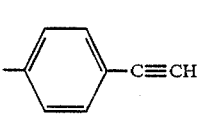 | yellow solid | purified by column chromatography | 1675 | 43.38  2.67  3.35<br>43.34  2.67  3.37 |

TABLE 1-continued

| No. | D | B | Form | Property (b.p.) | ir (cm⁻¹) (C=O) | Elemental analysis values (%) C | H | N |
|---|---|---|---|---|---|---|---|---|
| 51 | 3,4-dichlorothiophen-2-yl | 2,6-dimethylphenyl | pale yellow solid | 165° C./ 0.20 mmHg | 1685 | 59.28 59.33 | 5.57 5.61 | 4.29 4.33 |
| 52 | 3,4-dichlorothiophen-2-yl | 2,6-diethylphenyl | pale yellow solid | 178° C./ 0.30 mmHg | 1685 | 56.49 56.54 | 5.31 5.35 | 4.09 4.12 |
| 53 | 4-bromothiophen-2-yl | 2,6-dimethylphenyl | pale yellow solid | 178° C./ 0.35 mmHg | 1640 | 48.17 48.33 | 3.90 4.06 | 3.79 3.76 |
| 54 | 4,5-dibromothiophen-2-yl | 2,6-dimethylphenyl | pale yellow solid | purified by column chromatography | 1655 | 39.63 39.89 | 2.90 3.12 | 3.09 3.10 |
| 55 | 3,4-dimethoxythiophen-2-yl | 2,6-diethylphenyl | orange solid | 188–191° C./ 0.2 mmHg | 1680 | 59.46 59.75 | 6.15 6.33 | 3.95 3.67 |
| 56 | 5-iodothiophen-2-yl | 2,6-dimethylphenyl | pale yellowish brown solid | purified by column chromatography | 1670 | 43.11 42.92 | 3.75 3.60 | 3.28 3.34 |
| 57 | (5-chlorothiophen-2-yl)(CH(CH₃))- | 2,6-dimethylphenyl | pale yellow solid | 145° C./ 0.15 mmHg | 1675 | 54.87 54.87 | 4.56 4.57 | 4.28 4.27 |

EXAMPLE 6

By the same method as described in Examples 1 to 4, the N-substituted-chloroacetanilides shown in Table 2 were synthesized. Table 2 summarizes the forms, boiling points, characteristic IR absorption values and elemental analysis values (the values at the top were those found and the values at the bottom were those calculated) of the synthesized N-substituted-chloroaceanilide compounds.

TABLE 2

| No. | Compound | Form | Property (b.p.) | ir (cm⁻¹) (C=O) | Elemental analysis values (%) | | |
|---|---|---|---|---|---|---|---|
| | | | | | C | H | N |
| 1 | (structure: 3-OCH₃-thienyl-CH(CH₃)-N(2,6-diMe-phenyl)(COCH₂Cl)) | pale yellow solid | 178° C./ 0.15 mmHg | 1670 | 60.40 / 60.42 | 5.95 / 5.98 | 4.13 / 4.15 |
| 2 | (structure: 3-Cl-thienyl-CH(CH₃)-N(2-OCH₃,6-Me-phenyl)(COCH₂Cl)) | pale yellow solid | 173° C./ 0.10 mmHg | 1665 | 53.63 / 53.63 | 4.78 / 4.79 | 3.90 / 3.91 |
| 3 | (structure: 3-CH₂OCH₃-thienyl-CH(CH₃)-N(2,5-diMe-phenyl)(COCH₂Cl)) | pale yellow solid | 181° C./ 0.15 mmHg | 1670 | 61.45 / 61.43 | 6.35 / 6.31 | 3.93 / 3.98 |
| 4 | (structure: 5-Br-thienyl-CH(CH₃)-N(2,6-diEt-phenyl)(COCH₂Cl)) | pale yellow solid | 182° C./ 0.10 mmHg | 1665 | 52.10 / 52.12 | 5.10 / 5.11 | 3.39 / 3.38 |

FORMULATION EXAMPLE 1

Wettable powder

Ten parts of N-[2'-(3'-methoxy)-thienylmethyl]-N-chloroaceto-2,6-dimethylanilide, 85 parts of a 2:1 mixture of Zieclite and Kunilite (tradenames for clay minerals made by Kunimine Company) and 5 parts of Sorpol 800A (tradename for a surfactant manufactured by Toho Chemical Co., Ltd.) were uniformly mixed and pulverized to form a 10% wettable powder.

FORMULATION EXAMPLE 2

Emulsifiable concentrate

Twenty parts of N-[2'-(5'-ethoxy)-thienylmethyl]-N-chloroaceto-2,6-diethylanilide, 70 parts of xylene and 10 parts of Sorpol 800A as a surfactant were mixed and dissolved to form a 20% emulsifiable concentrate.

FORMULATION EXAMPLE 3

Five parts of N-[2'-(3'-chloro)-thienylmethyl]-N-chloroaceto-2-methyl-6-isopropylanilide, 50 parts of bentonite, 40 parts of Kunilite and 5 parts of Sorpol 800A as a surfactant were uniformly mixed and pulverized, and water was added. The mixture was uniformly stirred to form a paste. The paste was extruded from a hole having a diameter of 0.7 mm, dried and cut to a length of 1 to 2 mm to form 5% granules.

EXAMPLE 7

Water was added to paddy soil (alluvial soil) and the mixture was stirred and filled in porcelain pots (1/8850 a). Seeds of paddy weeds were sown in the pots and then rice seedlings (variety: akinishiki) in the three-leaf stage were transplanted in the pots to a depth of 2 cm. Water was added to provide a flooded state with a depth of 3 cm. A dilution of a wettable powder of each of the test compounds indicated in Table 3, prepared as in Formulation Example 1, was dripped onto the pots in a predetermined amount during the germination of the weeds. After this treatment, the plants were grown in a greenhouse at an average atmospheric temperature of 25° C. Three weeks later, the herbicidal effects of the test compounds were examined, and the results are shown in Table 3. The broad-leaved weeds shown in the table were false pimpernel (*Lindernia pyxidaria* L.), *Rotala indica* Koehne, and *Vandellia angustifolia* Benth.

In Table 3, compounds Nos. 66 to 71 are known compounds which were subjected to the same weed killing test as above for comparative purposes.

The herbicidal efficacy was rated on a scale of 0 to 5 as follows:

| Rating | Weed control ratio (%) |
|---|---|
| 0 | 0–9 |
| 1 | 10–29 |
| 2 | 30–49 |
| 3 | 50–69 |
| 4 | 70–89 |
| 5 | 90–100 |

In determining the phytotoxicity of each test compound to the transplanted rice, the height of the rice, the number of tillers from the rice and the total weight (dry weight) of the rice were measured, and the ratios of each of these to each of those of a non-treated area were calculated. The lowest ratio was selected among the ratios of the three factors, and the phytotoxicity to rice was rated on a scale of 0 to 5 as follows:

| Rating | Ratio to the non-treated area (%) |
|---|---|
| 0 | 100 |
| 1 | 90–99 |
| 2 | 80–89 |
| 3 | 60–79 |
| 4 | 40–59 |
| 5 | 0–39 |

TABLE 3

| No. | Compound | Dosage g/10a | Phytotoxicity to transplanted rice | Barnyard grass | Umbrella plant | Three-square grass | Monochoria | Broad-leaved weeds |
|---|---|---|---|---|---|---|---|---|
| 1 | (structure) | 1.5 | 0 | 5 | 5 | 4 | 4 | 5 |
|   |   | 3.0 | 0 | 5 | 5 | 5 | 5 | 5 |
|   |   | 7.5 | 0 | 5 | 5 | 5 | 5 | 5 |
|   |   | 15 | 0 | 5 | 5 | 5 | 5 | 5 |
|   |   | 30 | 0 | 5 | 5 | 5 | 5 | 5 |
|   |   | 60 | 0 | 5 | 5 | 5 | 5 | 5 |
|   |   | 125 | 0 | 5 | 5 | 5 | 5 | 5 |
|   |   | 250 | 0 | 5 | 5 | 5 | 5 | 5 |
|   |   | 500 | 0 | 5 | 5 | 5 | 5 | 5 |
|   |   | 1000 | 0 | 5 | 5 | 5 | 5 | 5 |
| 2 | (structure) | 1.5 | 0 | 5 | 5 | 3 | 3 | 4 |
|   |   | 3.0 | 0 | 5 | 5 | 5 | 4 | 5 |
|   |   | 7.5 | 0 | 5 | 5 | 5 | 5 | 5 |
|   |   | 15 | 0 | 5 | 5 | 5 | 5 | 5 |
|   |   | 30 | 0 | 5 | 5 | 5 | 5 | 5 |
|   |   | 60 | 0 | 5 | 5 | 5 | 5 | 5 |
|   |   | 125 | 0 | 5 | 5 | 5 | 5 | 5 |
|   |   | 250 | 0 | 5 | 5 | 5 | 5 | 5 |
|   |   | 500 | 0 | 5 | 5 | 5 | 5 | 5 |
|   |   | 1000 | 0 | 5 | 5 | 5 | 5 | 5 |
| 3 | (structure) | 125 | 0 | 5 | 5 | 5 | 5 | 5 |
|   |   | 250 | 0 | 5 | 5 | 5 | 5 | 5 |
|   |   | 500 | 0 | 5 | 5 | 5 | 5 | 5 |
| 4 | (structure) | 125 | 0 | 5 | 5 | 5 | 5 | 5 |
|   |   | 250 | 0 | 5 | 5 | 5 | 5 | 5 |
|   |   | 500 | 0 | 5 | 5 | 5 | 5 | 5 |
| 5 | (structure) | 125 | 0 | 5 | 5 | 4 | 5 | 5 |
|   |   | 250 | 0 | 5 | 5 | 5 | 5 | 5 |
|   |   | 500 | 0 | 5 | 5 | 5 | 5 | 5 |
| 6 | (structure) | 125 | 0 | 5 | 5 | 3 | 3 | 4 |
|   |   | 250 | 0 | 5 | 5 | 4 | 4 | 5 |
|   |   | 500 | 0 | 5 | 5 | 5 | 5 | 5 |

TABLE 3-continued

| No. | Compound | Dosage g/10a | Phytotoxicity to trans- planted rice | Barnyard grass | Umbrella plant | Three- square grass | Monochoria | Broad- leaved weeds |
|---|---|---|---|---|---|---|---|---|
| 7 | H₃CO—S—CH=CH—CH₂—N(COCH₂Cl)(2-Cl-C₆H₄) | 125<br>250<br>500 | 0<br>0<br>0 | 5<br>5<br>5 | 5<br>5<br>5 | 2<br>2<br>5 | 2<br>3<br>5 | 3<br>4<br>5 |
| 8 | H₃CO—S—CH=CH—CH₂—N(COCH₂Cl)(3-Br-C₆H₄) | 125<br>250<br>500 | 0<br>0<br>0 | 5<br>5<br>5 | 5<br>5<br>5 | 2<br>5<br>5 | 3<br>5<br>5 | 5<br>5<br>5 |
| 9 | H₃CO—S—CH=CH—CH₂—N(COCH₂Cl)(2,6-(CH₃)₂-C₆H₃) | 125<br>250<br>500 | 0<br>0<br>0 | 5<br>5<br>5 | 5<br>5<br>5 | 5<br>5<br>5 | 5<br>5<br>5 | 5<br>5<br>5 |
| 10 | H₃CO—S—CH=CH—CH₂—N(COCH₂Cl)(2-CH₃,6-C₂H₅-C₆H₃) | 125<br>250<br>500 | 0<br>0<br>0 | 5<br>5<br>5 | 5<br>5<br>5 | 5<br>5<br>5 | 5<br>5<br>5 | 5<br>5<br>5 |
| 11 | H₃CO—S—CH=CH—CH₂—N(COCH₂Cl)(2,6-(C₂H₅)₂-C₆H₃) | 125<br>250<br>500 | 0<br>0<br>0 | 5<br>5<br>5 | 5<br>5<br>5 | 5<br>5<br>5 | 5<br>5<br>5 | 5<br>5<br>5 |
| 12 | H₃CO—S—CH=CH—CH₂—N(COCH₂Cl)(2,4,6-(CH₃)₃-C₆H₂) | 125<br>250<br>500 | 0<br>0<br>0 | 5<br>5<br>5 | 4<br>4<br>5 | 2<br>4<br>5 | 2<br>2<br>3 | 3<br>4<br>5 |
| 13 | H₃CO—S—CH=CH—CH₂—N(COCH₂Cl)(2-CH(CH₃)₂,6-CH₃-C₆H₃) | 125<br>250<br>500 | 0<br>0<br>0 | 5<br>5<br>5 | 5<br>5<br>5 | 5<br>5<br>5 | 5<br>5<br>5 | 5<br>5<br>5 |
| 14 | H₃CO—S—CH=CH—CH₂—N(COCH₂Cl)(2-CH(CH₃)₂,6-C₂H₅-C₆H₃) | 125<br>250<br>500 | 0<br>0<br>0 | 5<br>5<br>5 | 5<br>5<br>5 | 4<br>5<br>5 | 5<br>5<br>5 | 5<br>5<br>5 |

TABLE 3-continued

| No. | Compound | Dosage g/10a | Phytotoxicity to trans-planted rice | Barnyard grass | Umbrella plant | Three-square grass | Monochoria | Broad-leaved weeds |
|---|---|---|---|---|---|---|---|---|
| 15 | H3CO-S-(thiophene)-CH2-N(2,6-diMe-C6H3)(COCH2Cl) | 125 | 0 | 5 | 5 | 5 | 5 | 5 |
|  |  | 250 | 0 | 5 | 5 | 5 | 5 | 5 |
|  |  | 500 | 0 | 5 | 5 | 5 | 5 | 5 |
| 16 | H3CS-S-(thiophene)-CH2-N(2,6-diMe-C6H3)(CHCH2Cl) | 125 | 0 | 5 | 5 | 5 | 4 | 4 |
|  |  | 250 | 0 | 5 | 5 | 5 | 5 | 5 |
|  |  | 500 | 0 | 5 | 5 | 5 | 5 | 5 |
| 17 | H3CS-S-(thiophene)-CH2-N(2,6-diEt-C6H3)(COCH2Cl) | 125 | 0 | 5 | 5 | 3 | 3 | 3 |
|  |  | 250 | 0 | 5 | 5 | 5 | 3 | 4 |
|  |  | 500 | 0 | 5 | 5 | 5 | 5 | 5 |
| 18 | H5C2O-S-(thiophene)-CH2-N(2,6-diF-C6H3)(COCH2Cl) | 125 | 0 | 5 | 4 | 3 | 1 | 3 |
|  |  | 250 | 0 | 5 | 5 | 3 | 2 | 4 |
|  |  | 500 | 0 | 5 | 5 | 4 | 4 | 5 |
| 19 | H5C2O-S-(thiophene)-CH2-N(2,6-diEt-C6H3)(COCH2Cl) | 125 | 0 | 5 | 5 | 5 | 4 | 5 |
|  |  | 250 | 0 | 5 | 5 | 5 | 5 | 5 |
|  |  | 500 | 0 | 5 | 5 | 5 | 5 | 5 |
| 20 | 3-OCH3-thiophene-2-CH2-N(2-Me-6-Et-C6H3)(COCH2Cl) | 125 | 0 | 5 | 5 | 5 | 5 | 5 |
|  |  | 250 | 0 | 5 | 5 | 5 | 5 | 5 |
|  |  | 500 | 0 | 5 | 5 | 5 | 5 | 5 |
| 21 | 3-OCH3-thiophene-2-CH2-N(2,6-diEt-C6H3)(COCH2Cl) | 125 | 0 | 5 | 5 | 5 | 5 | 5 |
|  |  | 250 | 0 | 5 | 5 | 5 | 5 | 5 |
|  |  | 500 | 0 | 5 | 5 | 5 | 5 | 5 |

TABLE 3-continued

| No. | Compound | Dosage g/10a | Phytotoxicity to trans- planted rice | Barnyard grass | Umbrella plant | Three- square grass | Monochoria | Broad- leaved weeds |
|---|---|---|---|---|---|---|---|---|
| 22 | (thiophene with OCH₃, CH₂-N-(2-Cl,6-CH₃-phenyl), COCH₂Cl) | 125 250 500 | 0 0 0 | 5 5 5 | 5 5 5 | 5 5 5 | 5 5 5 | 5 5 5 |
| 23 | (thiophene with OCH₃, CH₂-N-(2-CH(CH₃)₂,6-CH₃-phenyl), COCH₂Cl) | 125 250 500 | 0 0 0 | 5 5 5 | 5 5 5 | 5 5 5 | 5 5 5 | 5 5 5 |
| 24 | (thiophene with OCH₃, CH₂-N-(2-C₂H₅,6-CH(CH₃)₂-phenyl), COCH₂Cl) | 125 250 500 | 0 0 0 | 5 5 5 | 5 5 5 | 5 5 5 | 5 5 5 | 5 5 5 |
| 25 | (5-Br-thiophene, CH₂-N-(2,6-di-CH₃-phenyl), COCH₂Cl) | 125 250 500 | 0 0 0 | 5 5 5 | 5 5 5 | 5 5 5 | 5 5 5 | 5 5 5 |
| 26 | (5-Br-thiophene, CH₂-N-(2,6-di-C₂H₅-phenyl), COCH₂Cl) | 125 250 500 | 0 0 0 | 5 5 5 | 5 5 5 | 4 5 5 | 5 5 5 | 5 5 5 |
| 27 | (5-Br-thiophene, CH₂-N-(2-CH₃,6-Cl-phenyl), COCH₂Cl) | 125 250 500 | 0 0 0 | 5 5 5 | 5 5 5 | 5 5 5 | 5 5 5 | 5 5 5 |
| 28 | (5-Br-thiophene, CH₂-N-(2-CH₃,6-OCH₃-phenyl), COCH₂Cl) | 125 250 500 | 0 0 0 | 5 5 5 | 5 5 5 | 5 5 5 | 5 5 5 | 5 5 5 |

TABLE 3-continued

| No. | Compound | Dosage g/10a | Phytotoxicity to trans-planted rice | Barnyard grass | Umbrella plant | Three-square grass | Monochoria | Broad-leaved weeds |
|---|---|---|---|---|---|---|---|---|
| 29 | 5-Cl-thiophen-2-yl-CH$_2$-N(COCH$_2$Cl)-(2,6-diMe-C$_6$H$_3$) | 125<br>250<br>500 | 0<br>0<br>0 | 5<br>5<br>5 | 5<br>5<br>5 | 5<br>5<br>5 | 5<br>5<br>5 | 5<br>5<br>5 |
| 30 | 5-Cl-thiophen-2-yl-CH$_2$-N(COCH$_2$Cl)-(2,6-diEt-C$_6$H$_3$) | 125<br>250<br>500 | 0<br>0<br>0 | 5<br>5<br>5 | 5<br>5<br>5 | 4<br>5<br>5 | 4<br>5<br>5 | 5<br>5<br>5 |
| 31 | 5-Cl-thiophen-2-yl-CH$_2$-N(COCH$_2$Cl)-(2-OMe-6-Me-C$_6$H$_3$) | 125<br>250<br>500 | 0<br>0<br>0 | 5<br>5<br>5 | 5<br>5<br>5 | 5<br>5<br>5 | 5<br>5<br>5 | 5<br>5<br>5 |
| 32 | 3-Cl-thiophen-2-yl-CH$_2$-N(COCH$_2$Cl)-(2,6-diMe-C$_6$H$_3$) | 125<br>250<br>500 | 0<br>0<br>0 | 5<br>5<br>5 | 5<br>5<br>5 | 5<br>5<br>5 | 5<br>5<br>5 | 5<br>5<br>5 |
| 33 | 3-Cl-thiophen-2-yl-CH$_2$-N(COCH$_2$Cl)-(2-Me-6-Et-C$_6$H$_3$) | 125<br>250<br>500 | 0<br>0<br>0 | 5<br>5<br>5 | 5<br>5<br>5 | 5<br>5<br>5 | 5<br>5<br>5 | 5<br>5<br>5 |
| 34 | 3-Cl-thiophen-2-yl-CH$_2$-N(COCH$_2$Cl)-(2,6-diEt-C$_6$H$_3$) | 125<br>250<br>500 | 0<br>0<br>0 | 5<br>5<br>5 | 5<br>5<br>5 | 3<br>5<br>5 | 4<br>5<br>5 | 4<br>5<br>5 |
| 35 | 3-Cl-thiophen-2-yl-CH$_2$-N(COCH$_2$Cl)-(2-iPr-6-Me-C$_6$H$_3$) | 125<br>250<br>500 | 0<br>0<br>0 | 5<br>5<br>5 | 5<br>5<br>5 | 4<br>5<br>5 | 3<br>4<br>5 | 4<br>5<br>5 |

TABLE 3-continued

| No. | Compound | Dosage g/10a | Phytotoxicity to trans- planted rice | Barnyard grass | Umbrella plant | Three- square grass | Monochoria | Broad- leaved weeds |
|---|---|---|---|---|---|---|---|---|
| 36 | Cl-thiophene-CH₂-N(COCH₂Cl)-(2-CH(CH₃)₂, 6-C₂H₅-phenyl) | 125 | 0 | 5 | 5 | 4 | 2 | 3 |
|  |  | 250 | 0 | 5 | 5 | 4 | 4 | 4 |
|  |  | 500 | 0 | 5 | 5 | 4 | 5 | 5 |
| 37 | Cl-thiophene-CH₂-N(COCH₂Cl)-(2-OC₂H₅, 6-CH₃-phenyl) | 125 | 0 | 5 | 5 | 4 | 4 | 4 |
|  |  | 250 | 0 | 5 | 5 | 4 | 5 | 5 |
|  |  | 500 | 0 | 5 | 5 | 5 | 5 | 5 |
| 38 | Br-thiophene-CH₂-N(COCH₂Cl)-(2,6-diCH₃-phenyl) | 125 | 0 | 5 | 5 | 5 | 5 | 5 |
|  |  | 250 | 0 | 5 | 5 | 5 | 5 | 5 |
|  |  | 500 | 0 | 5 | 5 | 5 | 5 | 5 |
| 39 | Br-thiophene-CH₂-N(COCH₂Cl)-(2-OCH₃, 6-CH₃-phenyl) | 125 | 0 | 5 | 5 | 5 | 5 | 5 |
|  |  | 250 | 0 | 5 | 5 | 5 | 5 | 5 |
|  |  | 500 | 0 | 5 | 5 | 5 | 5 | 5 |
| 40 | H₃CO-thiophene-CH₂-N(COCH₂Cl)-(2-OCH(CH₃)₂, 6-CH₃-phenyl) | 125 | 0 | 5 | 5 | 3 | 5 | 5 |
|  |  | 250 | 0 | 5 | 5 | 5 | 5 | 5 |
|  |  | 500 | 0 | 5 | 5 | 5 | 5 | 5 |
| 41 | I-thiophene-CH₂-N(COCH₂Cl)-(4-CH(CH₃)₂-phenyl) | 125 | 0 | 4 | 4 | 2 | 2 | 3 |
|  |  | 250 | 0 | 5 | 5 | 2 | 3 | 3 |
|  |  | 500 | 0 | 5 | 5 | 3 | 4 | 3 |
| 42 | OC(CH₃)₃-thiophene-CH₂-N(COCH₂Cl)-(3-(CH₂)₃CH₃-phenyl) | 125 | 0 | 4 | 4 | 1 | 0 | 2 |
|  |  | 250 | 0 | 4 | 5 | 2 | 2 | 3 |
|  |  | 500 | 0 | 5 | 5 | 3 | 3 | 3 |

TABLE 3-continued

| No. | Compound | Dosage g/10a | Phytotoxicity to trans- planted rice | Barnyard grass | Umbrella plant | Three- square grass | Monochoria | Broad- leaved weeds |
|---|---|---|---|---|---|---|---|---|
| 43 | (3-F-thienyl)-CH₂-N(COCH₂Cl)-(2-CH₂CH=CH₂-phenyl) | 125 | 0 | 4 | 4 | 3 | 3 | 3 |
|   |   | 250 | 0 | 5 | 5 | 3 | 3 | 4 |
|   |   | 500 | 0 | 5 | 5 | 5 | 3 | 4 |
| 44 | (3-O(CH₂)₂CH₃-thienyl)-CH₂-N(COCH₂Cl)-(4-(CH₂)₅CH₃-phenyl) | 125 | 0 | 4 | 4 | 0 | 0 | 2 |
|   |   | 250 | 0 | 5 | 5 | 2 | 1 | 3 |
|   |   | 500 | 0 | 5 | 5 | 2 | 3 | 3 |
| 45 | (3-SCH₃-thienyl)-CH₂-N(COCH₂Cl)-(2,6-diCH₃-phenyl) | 125 | 0 | 5 | 5 | 5 | 5 | 5 |
|   |   | 250 | 0 | 5 | 5 | 5 | 5 | 5 |
|   |   | 500 | 0 | 5 | 5 | 5 | 5 | 5 |
| 46 | (5-OCH₂CH=CH₂-thienyl)-CH₂-N(COCH₂Cl)-(2-C(CH₃)₂-phenyl) | 125 | 0 | 4 | 4 | 1 | 0 | 1 |
|   |   | 250 | 0 | 4 | 5 | 2 | 0 | 3 |
|   |   | 500 | 0 | 5 | 5 | 3 | 3 | 4 |
| 47 | (4-I-thienyl)-CH₂-N(COCH₂Cl)-(4-C≡CH-phenyl) | 125 | 0 | 4 | 4 | 0 | 0 | 1 |
|   |   | 250 | 0 | 5 | 4 | 2 | 1 | 2 |
|   |   | 500 | 0 | 5 | 5 | 3 | 3 | 3 |
| 48 | (5-CH₃OCH₂-thienyl)-CH₂-N(COCH₂Cl)-(2,6-diCH₃-phenyl) | 125 | 0 | 5 | 5 | 5 | 5 | 5 |
|   |   | 250 | 0 | 5 | 5 | 5 | 5 | 5 |
|   |   | 500 | 0 | 5 | 5 | 5 | 5 | 5 |
| 49 | (3-CH₂OCH₃-thienyl)-CH₂-N(COCH₂Cl)-(2,6-diCH₃-phenyl) | 125 | 0 | 5 | 5 | 5 | 5 | 5 |
|   |   | 250 | 0 | 5 | 5 | 5 | 5 | 5 |
|   |   | 500 | 0 | 5 | 5 | 5 | 5 | 5 |
| 50 | (3-OCH₃-thienyl)-CH₂-N(COCH₂Cl)-(2,5-diCH₃-phenyl) | 125 | 0 | 5 | 5 | 5 | 5 | 5 |
|   |   | 250 | 0 | 5 | 5 | 5 | 5 | 5 |
|   |   | 500 | 0 | 5 | 5 | 5 | 5 | 5 |

TABLE 3-continued

| No. | Compound | Dosage g/10a | Phytotoxicity to transplanted rice | Barnyard grass | Umbrella plant | Three-square grass | Monochoria | Broad-leaved weeds |
|---|---|---|---|---|---|---|---|---|
| 51 | (3-OCH₃-thiophene-2-CH₂-N(COCH₂Cl)-2-CH₃-6-OCH₃-phenyl) | 125 | 0 | 5 | 5 | 5 | 5 | 5 |
|    |    | 250 | 0 | 5 | 5 | 5 | 5 | 5 |
|    |    | 500 | 0 | 5 | 5 | 5 | 5 | 5 |
| 52 | (3-SCH₃-thiophene-2-CH₂-N(COCH₂Cl)-2-CH₃-6-C₂H₅-phenyl) | 125 | 0 | 5 | 5 | 4 | 4 | 5 |
|    |    | 250 | 0 | 5 | 5 | 5 | 5 | 5 |
|    |    | 500 | 0 | 5 | 5 | 5 | 5 | 5 |
| 53 | (3-SCH₃-thiophene-2-CH₂-N(COCH₂Cl)-2,6-di-C₂H₅-phenyl) | 125 | 0 | 5 | 5 | 4 | 4 | 5 |
|    |    | 250 | 0 | 5 | 5 | 5 | 5 | 5 |
|    |    | 500 | 0 | 5 | 5 | 5 | 5 | 5 |
| 54 | (3-SC₂H₅-thiophene-2-CH₂-N(COCH₂Cl)-2,6-di-CH₃-phenyl) | 125 | 0 | 5 | 5 | 3 | 3 | 4 |
|    |    | 250 | 0 | 5 | 5 | 4 | 4 | 5 |
|    |    | 500 | 0 | 5 | 5 | 5 | 5 | 5 |
| 55 | (3,4-di-Cl-thiophene-2-CH₂-N(COCH₂Cl)-2,6-di-CH₃-phenyl) | 125 | 0 | 4 | 4 | 3 | 4 | 5 |
|    |    | 250 | 0 | 5 | 5 | 3 | 5 | 5 |
|    |    | 500 | 0 | 5 | 5 | 5 | 5 | 5 |
| 56 | (3,4-di-Cl-thiophene-2-CH₂-N(COCH₂Cl)-2,6-di-C₂H₅-phenyl) | 125 | 0 | 3 | 3 | 3 | 4 | 4 |
|    |    | 250 | 0 | 5 | 4 | 3 | 5 | 5 |
|    |    | 500 | 0 | 5 | 5 | 5 | 5 | 5 |
| 57 | (4-Br-thiophene-2-CH₂-N(COCH₂Cl)-2,6-di-CH₃-phenyl) | 125 | 0 | 5 | 5 | 5 | 5 | 5 |
|    |    | 250 | 0 | 5 | 5 | 5 | 5 | 5 |
|    |    | 500 | 0 | 5 | 5 | 5 | 5 | 5 |

TABLE 3-continued

| No. | Compound | Dosage g/10a | Phytotoxicity to trans- planted rice | Barnyard grass | Umbrella plant | Three- square grass | Monochoria | Broad- leaved weeds |
|---|---|---|---|---|---|---|---|---|
| 58 | (Br, Br-thiophene-CH₂-N(COCH₂Cl)(2,6-dimethylphenyl)) | 125 | 0 | 4 | 4 | 3 | 4 | 3 |
|  |  | 250 | 0 | 4 | 5 | 4 | 4 | 4 |
|  |  | 500 | 0 | 5 | 5 | 4 | 4 | 5 |
| 59 | (3,4-dimethoxythiophene-CH₂-N(COCH₂Cl)(2,6-diethylphenyl)) | 125 | 0 | 5 | 5 | 4 | 4 | 4 |
|  |  | 250 | 0 | 5 | 5 | 4 | 5 | 5 |
|  |  | 500 | 0 | 5 | 5 | 5 | 5 | 5 |
| 60 | (5-iodothiophene-CH₂-N(COCH₂Cl)(2,6-dimethylphenyl)) | 125 | 0 | 4 | 5 | 3 | 4 | 4 |
|  |  | 250 | 0 | 5 | 5 | 4 | 4 | 4 |
|  |  | 500 | 0 | 5 | 5 | 5 | 5 | 5 |
| 61 | (5-chlorothiophene-CH(CH₃)-N(COCH₂Cl)(2-methylphenyl)) | 125 | 0 | 5 | 5 | 5 | 5 | 5 |
|  |  | 250 | 0 | 5 | 5 | 5 | 5 | 5 |
|  |  | 500 | 0 | 5 | 5 | 5 | 5 | 5 |
| 62 | (3-methoxythiophene-CH(CH₃)-N(COCH₂Cl)(2,6-dimethylphenyl)) | 125 | 0 | 5 | 5 | 5 | 5 | 5 |
|  |  | 250 | 0 | 5 | 5 | 5 | 5 | 5 |
|  |  | 500 | 0 | 5 | 5 | 5 | 5 | 5 |
| 63 | (3-chlorothiophene-CH(CH₃)-N(COCH₂Cl)(2-methoxy-6-methylphenyl)) | 125 | 0 | 5 | 5 | 5 | 5 | 5 |
|  |  | 250 | 0 | 5 | 5 | 5 | 5 | 5 |
|  |  | 500 | 0 | 5 | 5 | 5 | 5 | 5 |
| 64 | (3-methoxymethylthiophene-CH(CH₃)-N(COCH₂Cl)(2,5-dimethylphenyl)) | 125 | 0 | 5 | 5 | 5 | 5 | 5 |
|  |  | 250 | 0 | 5 | 5 | 5 | 5 | 5 |
|  |  | 500 | 0 | 5 | 5 | 5 | 5 | 5 |

TABLE 3-continued

| No. | Compound | Dosage g/10a | Phytotoxicity to transplanted rice | Barnyard grass | Umbrella plant | Three-square grass | Monochoria | Broad-leaved weeds |
|---|---|---|---|---|---|---|---|---|
| 65 | Br-thiophene-CH(CH₃)-N(2,6-diethylphenyl)(COCH₂Cl) | 125<br>250<br>500 | 0<br>0<br>0 | 5<br>5<br>5 | 5<br>5<br>5 | 4<br>5<br>5 | 4<br>5<br>5 | 5<br>5<br>5 |
| 66 | thiophene-CH₂-N(2,6-dimethylphenyl)(COCH₂Cl) | 125<br>250<br>500 | 3<br>4<br>5 | 5<br>5<br>5 | 5<br>5<br>5 | 5<br>5<br>5 | 5<br>5<br>5 | 5<br>5<br>5 |
| 67 | thiophene-CH₂-N(2,6-diethylphenyl)(COCH₂Cl) | 125<br>250<br>500 | 2<br>2<br>3 | 5<br>5<br>5 | 5<br>5<br>5 | 5<br>5<br>5 | 5<br>5<br>5 | 5<br>5<br>5 |
| 68 | thiophene-CH₂-N(2-methyl-6-ethylphenyl)(COCH₂Cl) | 125<br>250<br>500 | 2<br>3<br>3 | 5<br>5<br>5 | 5<br>5<br>5 | 5<br>5<br>5 | 5<br>5<br>5 | 5<br>5<br>5 |
| 69 | 3-methylthiophene-CH₂-N(2,6-dimethylphenyl)(COCH₂Cl) | 125<br>250<br>500 | 2<br>3<br>4 | 5<br>5<br>5 | 5<br>5<br>5 | 5<br>5<br>5 | 5<br>5<br>5 | 5<br>5<br>5 |
| 70 | NO₂-thiophene-CH₂-N(2,6-diethylphenyl)(COCH₂Cl) | 125<br>250<br>500 | 0<br>0<br>0 | 0<br>0<br>2 | 0<br>1<br>2 | 0<br>0<br>0 | 0<br>0<br>0 | 0<br>0<br>0 |
| 71 | C₄H₉-O-CH₂-N(2,6-diethylphenyl)(COCH₂Cl) (Butachlor) | 125<br>250<br>500 | 1<br>2<br>3 | 5<br>5<br>5 | 5<br>5<br>5 | 5<br>5<br>5 | 5<br>5<br>5 | 5<br>5<br>5 |

EXAMPLE 8

Water was added to paddy soil (alluvial soil) and the mixture was stirred and filled in porcelain pots (1/8850 a). Seeds of barnyard grass were sown in the pots, and rice seedlings (variety: ayanishiki) in the 1.5-leave sage were transplanted in the pots to a depth of 2 cm. Tubers (terminal buds) of *Cyperus serotinus* Rottr. were buried in the surface layer of the soil, and water was added to provide a flooded state with a depth of 3 cm. An aqueous solution of a wettable powder of each of the test compounds, prepared in accordance with Formulation Example 1, was applied in a predetermined amount to the pots when the barnyard grass grew to a 0-leaf stage (during germination), a 1.5-leaf stage and 2.5-leaf stage, respectively. The pots were maintained in a greenhouse at an average atmospheric temperature of 25° C., and 3 weeks later, the herbicidal effects of the test compounds were examined. The results are shown in Table 4 together with those obtained by using known compounds (Nos. 12 to 15 and 34 and 35).

The degree of growth of *Cyperus serotinus* in the table is shown by its height (cm). The herbicidal effects were rated on the same scale as in Example 7.

TABLE 4

| No. | Compound | Dosage g/10a | Phytotoxicity to paddy rice | | | Herbicidal activity on barnyard grass | | | Herbicidal activity on *Cyperus serotinus* | | |
|---|---|---|---|---|---|---|---|---|---|---|---|
| | | | 1.5-leaf | 3-leaf | 4-leaf | 0-leaf | 1.5-leaf | 2.5-leaf | 0 cm | 5–8 cm | 10–15 cm |
| 1 | [structure: thiophene-OCH₃, CH₂-N(COCH₂Cl)-(2,6-dimethylphenyl)] | 30 | 0 | 0 | 0 | 5 | 5 | 3 | 5 | 5 | 3 |
| | | 60 | 0 | 0 | 0 | 5 | 5 | 5 | 5 | 5 | 4 |
| | | 125 | 0 | 0 | 0 | 5 | 5 | 5 | 5 | 5 | 5 |
| | | 250 | 0 | 0 | 0 | 5 | 5 | 5 | 5 | 5 | 5 |
| | | 500 | 0 | 0 | 0 | 5 | 5 | 5 | 5 | 5 | 5 |
| 2 | [structure: thiophene-Cl, CH₂-N(COCH₂Cl)-(2-OCH₃, 6-CH₃-phenyl)] | 125 | 0 | 0 | 0 | 5 | 5 | 5 | 5 | 5 | 3 |
| | | 250 | 0 | 0 | 0 | 5 | 5 | 5 | 5 | 5 | 4 |
| | | 500 | 0 | 0 | 0 | 5 | 5 | 5 | 5 | 5 | 5 |
| 3 | [structure: H₃CO-thiophene-CH₂-N(COCH₂Cl)-(2,6-dimethylphenyl)] | 125 | 0 | 0 | 0 | 5 | 5 | 3 | 5 | 2 | 0 |
| | | 250 | 0 | 0 | 0 | 5 | 5 | 4 | 5 | 4 | 2 |
| | | 500 | 0 | 0 | 0 | 5 | 5 | 5 | 5 | 5 | 5 |
| 4 | [structure: H₃CO-thiophene-CH₂-N(OCH₃,COCH₂Cl)-(2-CH₃-phenyl)] | 125 | 0 | 0 | 0 | 5 | 5 | 3 | 5 | 3 | 0 |
| | | 250 | 0 | 0 | 0 | 5 | 5 | 5 | 5 | 5 | 2 |
| | | 500 | 0 | 0 | 0 | 5 | 5 | 5 | 5 | 5 | 3 |
| 5 | [structure: thiophene-OCH₃, CH₂-N(C₂H₅,COCH₂Cl)-(2-CH₃-phenyl)] | 125 | 0 | 0 | 0 | 5 | 5 | 5 | 5 | 5 | 4 |
| | | 250 | 0 | 0 | 0 | 5 | 5 | 5 | 5 | 5 | 4 |
| | | 500 | 0 | 0 | 0 | 5 | 5 | 5 | 5 | 5 | 5 |
| 6 | [structure: thiophene-OCH₃, CH₂-N(Cl,COCH₂Cl)-(2-CH₃-phenyl)] | 125 | 0 | 0 | 0 | 5 | 5 | 5 | 5 | 5 | 3 |
| | | 250 | 0 | 0 | 0 | 5 | 5 | 5 | 5 | 5 | 4 |
| | | 500 | 0 | 0 | 0 | 5 | 5 | 5 | 5 | 5 | 5 |

TABLE 4-continued

| No. | Compound | Dosage g/10a | Phytotoxicity to paddy rice | | | Herbicidal activity on barnyard grass | | | Herbicidal activity on Cyperus serotinus | | |
|---|---|---|---|---|---|---|---|---|---|---|---|
| | | | 1.5-leaf | 3-leaf | 4-leaf | 0-leaf | 1.5-leaf | 2.5-leaf | 0 cm | 5–8 cm | 10–15 cm |
| 7 | Cl-thiophene-CH₂-N(2,6-diMe-C₆H₃)(COCH₂Cl) | 125 | 0 | 0 | 0 | 5 | 5 | 3 | 5 | 2 | 0 |
| | | 250 | 0 | 0 | 0 | 5 | 5 | 3 | 5 | 3 | 0 |
| | | 500 | 0 | 0 | 0 | 5 | 5 | 4 | 5 | 4 | 3 |
| 8 | Cl-thiophene-CH₂-N(2-OMe-6-Me-C₆H₃)(COCH₂Cl) | 125 | 0 | 0 | 0 | 5 | 5 | 3 | 5 | 0 | 0 |
| | | 250 | 0 | 0 | 0 | 5 | 5 | 4 | 5 | 2 | 0 |
| | | 500 | 0 | 0 | 0 | 5 | 5 | 4 | 5 | 3 | 1 |
| 9 | 3-Cl-thiophene-CH₂-N(2,6-diMe-C₆H₃)(COCH₂Cl) | 125 | 0 | 0 | 0 | 5 | 5 | 3 | 5 | 0 | 0 |
| | | 250 | 0 | 0 | 0 | 5 | 5 | 3 | 5 | 0 | 0 |
| | | 500 | 0 | 0 | 0 | 5 | 5 | 3 | 5 | 4 | 2 |
| 10 | Br-thiophene-CH₂-N(2-OMe-6-Me-C₆H₃)(COCH₂Cl) | 125 | 0 | 0 | 0 | 5 | 5 | 3 | 5 | 0 | 0 |
| | | 250 | 0 | 0 | 0 | 5 | 5 | 3 | 5 | 2 | 0 |
| | | 500 | 0 | 0 | 0 | 5 | 5 | 4 | 5 | 5 | 3 |
| 11 | SCH₃-thiophene-CH₂-N(2,6-diMe-C₆H₃)(COCH₂Cl) | 125 | 0 | 0 | 0 | 5 | 5 | 3 | 5 | 5 | 4 |
| | | 250 | 0 | 0 | 0 | 5 | 5 | 4 | 5 | 5 | 4 |
| | | 500 | 0 | 0 | 0 | 5 | 5 | 5 | 5 | 5 | 5 |
| 12 | C₄H₉OCH₂-N(2,6-diEt-C₆H₃)(COCH₂Cl) (butachlor) | 125 | 1 | 0 | 0 | 5 | 4 | 1 | 3 | 0 | 0 |
| | | 250 | 2 | 1 | 0 | 5 | 5 | 2 | 5 | 1 | 0 |
| | | 500 | 3 | 1 | 0 | 5 | 5 | 3 | 5 | 3 | 0 |
| 13 | thiophene-CH₂-N(2-Me-6-Et-C₆H₃)(COCH₂Cl) | 125 | 2 | 0 | 0 | 5 | 2 | 0 | 2 | 0 | 0 |
| | | 250 | 3 | 1 | 0 | 5 | 3 | 0 | 3 | 0 | 0 |
| | | 500 | 3 | 2 | 0 | 5 | 5 | 2 | 3 | 0 | 0 |

TABLE 4-continued

| No. | Compound | Dosage g/10a | Phytotoxicity to paddy rice | | | Herbicidal activity on barnyard grass | | | Herbicidal activity on Cyperus serotinus | | |
|---|---|---|---|---|---|---|---|---|---|---|---|
| | | | 1.5-leaf | 3-leaf | 4-leaf | 0-leaf | 1.5-leaf | 2.5-leaf | 0 cm | 5-8 cm | 10-15 cm |
| 14 | [thiophene-CH₃, CH₂-N(2,6-dimethylphenyl)(COCH₂Cl)] | 125 | 2 | 0 | 0 | 5 | 3 | 0 | 3 | 0 | 0 |
| | | 250 | 3 | 2 | 0 | 5 | 4 | 1 | 3 | 0 | 0 |
| | | 500 | 4 | 3 | 1 | 5 | 5 | 2 | 4 | 0 | 0 |
| 15 | [O₂N-thiophene-CH₂-N(2,6-diethylphenyl)(COCH₂Cl)] | 125 | 0 | 0 | 0 | 0 | 0 | 0 | 0 | 0 | 0 |
| | | 250 | 0 | 0 | 0 | 0 | 0 | 0 | 0 | 0 | 0 |
| | | 500 | 0 | 0 | 0 | 2 | 0 | 0 | 0 | 0 | 0 |
| 16 | [CH₃OCH₂-thiophene-CH₂-N(2,6-dimethylphenyl)(COCH₂Cl)] | 125 | 0 | 0 | 0 | 5 | 5 | 3 | 3 | 0 | 0 |
| | | 250 | 0 | 0 | 0 | 5 | 5 | 5 | 4 | 1 | 0 |
| | | 500 | 0 | 0 | 0 | 5 | 5 | 5 | 4 | 3 | 0 |
| 17 | [CH₂OCH₃-thiophene-CH₂-N(2,6-dimethylphenyl)(COCH₂Cl)] | 125 | 0 | 0 | 0 | 5 | 5 | 3 | 3 | 0 | 0 |
| | | 250 | 0 | 0 | 0 | 5 | 5 | 4 | 3 | 2 | 0 |
| | | 500 | 0 | 0 | 0 | 5 | 5 | 5 | 5 | 2 | 0 |
| 18 | [OCH₃-thiophene-CH₂-N(3,5-dimethylphenyl)(COCH₂Cl)] | 125 | 0 | 0 | 0 | 5 | 5 | 4 | 3 | 0 | 0 |
| | | 250 | 0 | 0 | 0 | 5 | 5 | 5 | 4 | 1 | 0 |
| | | 500 | 0 | 0 | 0 | 5 | 5 | 5 | 5 | 2 | 0 |
| 19 | [OCH₃-thiophene-CH₂-N(2-OCH₃,6-CH₃-phenyl)(COCH₂Cl)] | 125 | 0 | 0 | 0 | 5 | 5 | 5 | 5 | 5 | 3 |
| | | 250 | 0 | 0 | 0 | 5 | 5 | 5 | 5 | 5 | 3 |
| | | 500 | 0 | 0 | 0 | 5 | 5 | 5 | 5 | 5 | 5 |
| 20 | [SCH₃-thiophene-CH₂-N(2-CH₃,6-C₂H₅-phenyl)(COCH₂Cl)] | 125 | 0 | 0 | 0 | 5 | 4 | 3 | 4 | 3 | 0 |
| | | 250 | 0 | 0 | 0 | 5 | 5 | 4 | 4 | 4 | 3 |
| | | 500 | 0 | 0 | 0 | 5 | 5 | 5 | 5 | 5 | 3 |

TABLE 4-continued

| No. | Compound | Dosage g/10a | Phytotoxicity to paddy rice 1.5-leaf | 3-leaf | 4-leaf | Herbicidal activity on barnyard grass 0-leaf | 1.5-leaf | 2.5-leaf | Herbicidal activity on Cyperus serotinus 0 cm | 5–8 cm | 10–15 cm |
|---|---|---|---|---|---|---|---|---|---|---|---|
| 21 | SCH₃, C₂H₅, thiophene–CH₂–N(2,6-diethylphenyl)(COCH₂Cl) | 125 / 250 / 500 | 0 / 0 / 0 | 0 / 0 / 0 | 0 / 0 / 0 | 5 / 5 / 5 | 3 / 4 / 5 | 0 / 2 / 3 | 5 / 5 / 5 | 3 / 4 / 5 | 1 / 2 / 3 |
| 22 | SC₂H₅, CH₃, thiophene–CH₂–N(2,6-dimethylphenyl)(COCH₂Cl) | 125 / 250 / 500 | 0 / 0 / 0 | 0 / 0 / 0 | 0 / 0 / 0 | 5 / 5 / 5 | 3 / 3 / 5 | 1 / 2 / 3 | 5 / 5 / 5 | 3 / 5 / 5 | 0 / 2 / 3 |
| 23 | 3,4-Cl₂-thiophene–CH₂–N(2,6-dimethylphenyl)(COCH₂Cl) | 125 / 250 / 500 | 0 / 0 / 0 | 0 / 0 / 0 | 0 / 0 / 0 | 4 / 5 / 5 | 3 / 3 / 3 | 0 / 1 / 2 | 1 / 2 / 3 | 0 / 0 / 2 | 0 / 0 / 0 |
| 24 | 3,4-Cl₂-thiophene–CH₂–N(2,6-diethylphenyl)(COCH₂Cl) | 125 / 250 / 500 | 0 / 0 / 0 | 0 / 0 / 0 | 0 / 0 / 0 | 3 / 5 / 5 | 1 / 2 / 3 | 0 / 0 / 2 | 1 / 1 / 3 | 0 / 0 / 2 | 0 / 0 / 0 |
| 25 | 4-Br-thiophene–CH₂–N(2,6-dimethylphenyl)(COCH₂Cl) | 125 / 250 / 500 | 0 / 0 / 0 | 0 / 0 / 0 | 0 / 0 / 0 | 5 / 5 / 5 | 5 / 5 / 5 | 4 / 5 / 5 | 5 / 5 / 5 | 2 / 4 / 5 | 0 / 1 / 3 |
| 26 | 4,5-Br₂-thiophene–CH₂–N(2,6-dimethylphenyl)(COCH₂Cl) | 125 / 250 / 500 | 0 / 0 / 0 | 0 / 0 / 0 | 0 / 0 / 0 | 4 / 4 / 5 | 3 / 4 / 4 | 0 / 1 / 2 | 2 / 3 / 5 | 1 / 1 / 3 | 0 / 0 / 0 |
| 27 | 3,4-(OCH₃)₂-thiophene–CH₂–N(2,6-diethylphenyl)(COCH₂Cl) | 125 / 250 / 500 | 0 / 0 / 0 | 0 / 0 / 0 | 0 / 0 / 0 | 5 / 5 / 5 | 3 / 4 / 5 | 3 / 3 / 3 | 3 / 4 / 5 | 0 / 0 / 2 | 0 / 0 / 1 |

TABLE 4-continued

| No. | Compound | Dosage g/10a | Phytotoxicity to paddy rice | | | Herbicidal activity on barnyard grass | | | Herbicidal activity on Cyperus serotinus | | |
|---|---|---|---|---|---|---|---|---|---|---|---|
| | | | 1.5-leaf | 3-leaf | 4-leaf | 0-leaf | 1.5-leaf | 2.5-leaf | 0 cm | 5-8 cm | 10-15 cm |
| 28 | [I-thiophene-CH₂-N(2,6-diMe-Ph)(COCH₂Cl)] | 125 | 0 | 0 | 0 | 4 | 4 | 3 | 4 | 1 | 0 |
| | | 250 | 0 | 0 | 0 | 5 | 5 | 3 | 5 | 2 | 0 |
| | | 500 | 0 | 0 | 0 | 5 | 5 | 5 | 5 | 3 | 0 |
| 29 | [Cl-thiophene-CH(CH₃)-N(2-Me-Ph)(COCH₂Cl)] | 125 | 0 | 0 | 0 | 5 | 5 | 3 | 5 | 4 | 3 |
| | | 250 | 0 | 0 | 0 | 5 | 5 | 5 | 5 | 4 | 3 |
| | | 500 | 0 | 0 | 0 | 5 | 5 | 5 | 5 | 5 | 5 |
| 30 | [OCH₃-thiophene-CH(CH₃)-N(2,6-diMe-Ph)(COCH₂Cl)] | 125 | 0 | 0 | 0 | 5 | 5 | 5 | 5 | 5 | 5 |
| | | 250 | 0 | 0 | 0 | 5 | 5 | 5 | 5 | 5 | 5 |
| | | 500 | 0 | 0 | 0 | 5 | 5 | 5 | 5 | 5 | 5 |
| 31 | [Cl-thiophene-CH(CH₃)-N(2-OCH₃,6-Me-Ph)(COCH₂Cl)] | 125 | 0 | 0 | 0 | 5 | 5 | 5 | 5 | 5 | 4 |
| | | 250 | 0 | 0 | 0 | 5 | 5 | 5 | 5 | 5 | 4 |
| | | 500 | 0 | 0 | 0 | 5 | 5 | 5 | 5 | 5 | 5 |
| 32 | [CH₂OCH₃-thiophene-CH(CH₃)-N(2,5-diMe-Ph)(COCH₂Cl)] | 125 | 0 | 0 | 0 | 5 | 5 | 3 | 5 | 4 | 3 |
| | | 250 | 0 | 0 | 0 | 5 | 5 | 4 | 5 | 5 | 4 |
| | | 500 | 0 | 0 | 0 | 5 | 5 | 5 | 5 | 5 | 5 |
| 33 | [Br-thiophene-CH(CH₃)-N(2,6-diEt-Ph)(COCH₂Cl)] | 125 | 0 | 0 | 0 | 5 | 4 | 2 | 3 | 1 | 0 |
| | | 250 | 0 | 0 | 0 | 5 | 5 | 3 | 4 | 2 | 0 |
| | | 500 | 0 | 0 | 0 | 5 | 5 | 5 | 5 | 3 | 2 |
| 34 | [thiophene-CH₂-N(2,6-diMe-Ph)(COCH₂Cl)] | 125 | 3 | 1 | 0 | 5 | 4 | 0 | 3 | 0 | 0 |
| | | 250 | 4 | 2 | 0 | 5 | 4 | 1 | 3 | 0 | 0 |
| | | 500 | 4 | 3 | 2 | 5 | 5 | 2 | 4 | 2 | 0 |

TABLE 4-continued

| No. | Compound | Dosage g/10a | Phytotoxicity to paddy rice 1.5-leaf | 3-leaf | 4-leaf | Herbicidal activity on barnyard grass 0-leaf | 1.5-leaf | 2.5-leaf | Herbicidal activity on *Cyperus serotinus* 0 cm | 5-8 cm | 10-15 cm |
|---|---|---|---|---|---|---|---|---|---|---|---|
| 35 | (thiophene)-CH$_2$-N(2,6-diethylphenyl)(COCH$_2$Cl) | 125 | 1 | 0 | 0 | 5 | 3 | 0 | 2 | 0 | 0 |
|  |  | 250 | 3 | 1 | 0 | 5 | 3 | 0 | 3 | 0 | 0 |
|  |  | 500 | 3 | 2 | 1 | 5 | 5 | 2 | 3 | 0 | 0 |

EXAMPLE 9

Porcelain pots (1/8850 a) were filled with upland farm soil (clay loam), and seeds of the plants shown in Table 5 were sown to a depth of 0.5 to 1 cm. An aqueous dilution of a wettable powder of each of the test compounds, prepared as in Formuation Example 1, was sprayed in a predetermined amount over the surface of the soil. After the treatment, the plants were allowed to grow in a greenhouse at an average atmospheric temperature of 25° C. Two weeks later, the herbicidal effects of the test compounds were examined. The results are shown in Table 5 together with those obtained with comparative compounds (Nos. 28 to 33). The phytotoxicity to crops and the herbicidal effects were rated on the same scales as in Example 7.

TABLE 5

| No. | Compound | Dosage g/10a | Phytotoxicity to crops Rice | Wheat | Corn | Soybean | Cotton | Herbicidal activity Barnyard grass | Large crabgrass | Green foxtail | Yellow-cyperus |
|---|---|---|---|---|---|---|---|---|---|---|---|
| 1 | 3-OCH$_3$-thiophene-CH$_2$-N(2,6-diCH$_3$-phenyl)(COCH$_2$Cl) | 100 | 0 | 0 | 0 | 0 | 0 | 5 | 5 | 5 | 5 |
|  |  | 200 | 0 | 0 | 0 | 0 | 0 | 5 | 5 | 5 | 5 |
|  |  | 400 | 0 | 2 | 0 | 0 | 0 | 5 | 5 | 5 | 5 |
| 2 | 3-Cl,4-OCH$_3$-thiophene-CH$_2$-N(2,6-diCH$_3$-phenyl)(COCH$_2$Cl) | 100 | 0 | 0 | 0 | 0 | 0 | 5 | 5 | 5 | 5 |
|  |  | 200 | 0 | 0 | 0 | 0 | 0 | 5 | 5 | 5 | 5 |
|  |  | 400 | 0 | 1 | 0 | 0 | 0 | 5 | 5 | 5 | 5 |
| 3 | 5-H$_3$CO-thiophene-CH$_2$-N(2,6-diCH$_3$-phenyl)(COCH$_2$Cl) | 100 | 0 | 0 | 0 | 0 | 0 | 5 | 4 | 4 | 5 |
|  |  | 200 | 0 | 0 | 0 | 0 | 0 | 5 | 5 | 5 | 5 |
|  |  | 400 | 0 | 0 | 0 | 0 | 0 | 5 | 5 | 5 | 5 |
| 4 | 3-OCH$_3$-thiophene-CH$_2$-N(2-CH$_3$,6-C$_2$H$_5$-phenyl)(COCH$_2$Cl) | 100 | 0 | 0 | 0 | 0 | 0 | 5 | 5 | 4 | 5 |
|  |  | 200 | 0 | 0 | 0 | 0 | 0 | 5 | 5 | 5 | 5 |
|  |  | 400 | 0 | 0 | 0 | 0 | 0 | 5 | 5 | 5 | 5 |

TABLE 5-continued

| No. | Compound | Dosage g/10a | Phytotoxicity to crops | | | | | Herbicidal activity | | | |
|---|---|---|---|---|---|---|---|---|---|---|---|
| | | | Rice | Wheat | Corn | Soybean | Cotton | Barnyard grass | Large crabgrass | Green foxtail | Yellowcyperus |
| 5 | [structure: thiophene with OCH₃, CH₂-N linked to 2-Cl-6-CH₃-phenyl, N-COCH₂Cl] | 100 | 0 | 0 | 0 | 0 | 0 | 5 | 5 | 5 | 5 |
| | | 200 | 0 | 1 | 0 | 0 | 0 | 5 | 5 | 5 | 5 |
| | | 400 | 0 | 2 | 0 | 0 | 0 | 5 | 5 | 5 | 5 |
| 6 | [structure: 5-Cl-thiophene, CH₂-N linked to 2,6-diCH₃-phenyl, N-COCH₂Cl] | 100 | 0 | 0 | 0 | 0 | 0 | 4 | 3 | 3 | 5 |
| | | 200 | 0 | 0 | 0 | 0 | 0 | 5 | 5 | 3 | 5 |
| | | 400 | 0 | 0 | 0 | 0 | 0 | 5 | 5 | 5 | 5 |
| 7 | [structure: 3-Cl-thiophene, CH₂-N linked to 2,6-diCH₃-phenyl, N-COCH₂Cl] | 100 | 0 | 0 | 0 | 0 | 0 | 5 | 5 | 4 | 5 |
| | | 200 | 0 | 0 | 0 | 0 | 0 | 5 | 5 | 5 | 5 |
| | | 400 | 0 | 0 | 0 | 0 | 0 | 5 | 5 | 5 | 5 |
| 8 | [structure: 4-Br-thiophene, CH₂-N linked to 2-OCH₃-6-CH₃-phenyl, N-COCH₂Cl] | 100 | 0 | 0 | 0 | 0 | 0 | 4 | 4 | 3 | 5 |
| | | 200 | 0 | 0 | 0 | 0 | 0 | 5 | 5 | 5 | 5 |
| | | 400 | 0 | 0 | 0 | 0 | 0 | 5 | 5 | 5 | 5 |
| 9 | [structure: 3-SCH₃-thiophene, CH₂-N linked to 2,6-diCH₃-phenyl, N-COCH₂Cl] | 100 | 0 | 0 | 0 | 0 | 0 | 5 | 5 | 4 | 5 |
| | | 200 | 0 | 0 | 0 | 0 | 0 | 5 | 5 | 5 | 5 |
| | | 400 | 0 | 0 | 0 | 0 | 0 | 5 | 5 | 5 | 5 |
| 10 | [structure: 5-CH₃OCH₂-thiophene, CH₂-N linked to 2,6-diCH₃-phenyl, N-COCH₂Cl] | 100 | 0 | 0 | 0 | 0 | 0 | 5 | 4 | 5 | 5 |
| | | 200 | 0 | 0 | 0 | 0 | 0 | 5 | 5 | 5 | 5 |
| | | 400 | 0 | 0 | 0 | 0 | 0 | 5 | 5 | 5 | 5 |

TABLE 5-continued

| No. | Compound | Dosage g/10a | Phytotoxicity to crops | | | | | Herbicidal activity | | | |
|---|---|---|---|---|---|---|---|---|---|---|---|
| | | | Rice | Wheat | Corn | Soybean | Cotton | Barnyard grass | Large crabgrass | Green foxtail | Yellow-cyperus |
| 11 | [thiophene with CH₂OCH₃ and CH₂-N(2,6-diMe-phenyl)(COCH₂Cl)] | 100 | 0 | 0 | 0 | 0 | 0 | 5 | 4 | 4 | 3 |
| | | 200 | 0 | 0 | 0 | 0 | 0 | 5 | 5 | 5 | 4 |
| | | 400 | 0 | 0 | 0 | 0 | 0 | 5 | 5 | 5 | 5 |
| 12 | [thiophene with OCH₃ and CH₂-N(2,5-diMe-phenyl)(COCH₂Cl)] | 100 | 0 | 0 | 0 | 0 | 0 | 5 | 5 | 5 | 3 |
| | | 200 | 0 | 0 | 0 | 0 | 0 | 5 | 5 | 5 | 3 |
| | | 400 | 0 | 0 | 0 | 0 | 0 | 5 | 5 | 5 | 5 |
| 13 | [thiophene with OCH₃ and CH₂-N(2-OCH₃-6-Me-phenyl)(COCH₂Cl)] | 100 | 0 | 0 | 0 | 0 | 0 | 5 | 5 | 5 | 5 |
| | | 200 | 0 | 0 | 0 | 0 | 0 | 5 | 5 | 5 | 5 |
| | | 400 | 0 | 0 | 0 | 0 | 0 | 5 | 5 | 5 | 5 |
| 14 | [thiophene with SCH₃ and CH₂-N(2-Me-6-C₂H₅-phenyl)(COCH₂Cl)] | 100 | 0 | 0 | 0 | 0 | 0 | 4 | 3 | 3 | 3 |
| | | 200 | 0 | 0 | 0 | 0 | 0 | 5 | 5 | 4 | 4 |
| | | 400 | 0 | 0 | 0 | 0 | 0 | 5 | 5 | 5 | 5 |
| 15 | [thiophene with SCH₃ and CH₂-N(2,6-di-C₂H₅-phenyl)(COCH₂Cl)] | 100 | 0 | 0 | 0 | 0 | 0 | 5 | 5 | 3 | 3 |
| | | 200 | 0 | 0 | 0 | 0 | 0 | 5 | 5 | 5 | 3 |
| | | 400 | 0 | 0 | 0 | 0 | 0 | 5 | 5 | 5 | 5 |
| 16 | [thiophene with SC₂H₅ and CH₂-N(2,6-diMe-phenyl)(COCH₂Cl)] | 100 | 0 | 0 | 0 | 0 | 0 | 4 | 4 | 4 | 4 |
| | | 200 | 0 | 0 | 0 | 0 | 0 | 5 | 4 | 5 | 4 |
| | | 400 | 0 | 0 | 0 | 0 | 0 | 5 | 5 | 5 | 5 |
| 17 | [3,4-dichlorothiophene with CH₂-N(2,6-diMe-phenyl)(COCH₂Cl)] | 100 | 0 | 0 | 0 | 0 | 0 | 3 | 3 | 3 | 3 |
| | | 200 | 0 | 0 | 0 | 0 | 0 | 4 | 3 | 4 | 4 |
| | | 400 | 0 | 0 | 0 | 0 | 0 | 5 | 4 | 4 | 4 |

TABLE 5-continued

| No. | Compound | Dosage g/10a | Phytotoxicity to crops ||||| Herbicidal activity ||||
| | | | Rice | Wheat | Corn | Soybean | Cotton | Barnyard grass | Large crabgrass | Green foxtail | Yellow-cyperus |
|---|---|---|---|---|---|---|---|---|---|---|---|
| 18 | 3,4-dichlorothiophene-CH₂-N(2,6-diethylphenyl)-COCH₂Cl | 100 | 0 | 0 | 0 | 0 | 0 | 3 | 3 | 2 | 3 |
| | | 200 | 0 | 0 | 0 | 0 | 0 | 3 | 4 | 4 | 4 |
| | | 400 | 0 | 0 | 0 | 0 | 0 | 5 | 5 | 4 | 4 |
| 19 | 4-bromothiophene-CH₂-N(2,6-dimethylphenyl)-COCH₂Cl | 100 | 0 | 0 | 0 | 0 | 0 | 5 | 5 | 5 | 5 |
| | | 200 | 0 | 0 | 0 | 0 | 0 | 5 | 5 | 5 | 5 |
| | | 400 | 0 | 0 | 0 | 0 | 0 | 5 | 5 | 5 | 5 |
| 20 | 4,5-dibromothiophene-CH₂-N(2,6-dimethylphenyl)-COCH₂Cl | 100 | 0 | 0 | 0 | 0 | 0 | 3 | 3 | 3 | 3 |
| | | 200 | 0 | 0 | 0 | 0 | 0 | 4 | 3 | 3 | 3 |
| | | 400 | 0 | 0 | 0 | 0 | 0 | 4 | 4 | 4 | 3 |
| 21 | 3,4-dimethoxythiophene-CH₂-N(2,6-diethylphenyl)-COCH₂Cl | 100 | 0 | 0 | 0 | 0 | 0 | 5 | 4 | 4 | 5 |
| | | 200 | 0 | 0 | 0 | 0 | 0 | 5 | 5 | 5 | 5 |
| | | 400 | 0 | 0 | 0 | 0 | 0 | 5 | 5 | 5 | 5 |
| 22 | 5-iodothiophene-CH₂-N(2,6-dimethylphenyl)-COCH₂Cl | 100 | 0 | 0 | 0 | 0 | 0 | 3 | 2 | 2 | 2 |
| | | 200 | 0 | 0 | 0 | 0 | 0 | 4 | 3 | 3 | 3 |
| | | 400 | 0 | 0 | 0 | 0 | 0 | 5 | 4 | 5 | 4 |
| 23 | 5-chlorothiophene-CH(CH₃)-N(2-methylphenyl)-COCH₂Cl | 100 | 0 | 0 | 0 | 0 | 0 | 5 | 4 | 5 | 5 |
| | | 200 | 0 | 0 | 0 | 0 | 0 | 5 | 5 | 5 | 5 |
| | | 400 | 0 | 0 | 0 | 0 | 0 | 5 | 5 | 5 | 5 |
| 24 | 3-methoxythiophene-CH(CH₃)-N(2,6-dimethylphenyl)-COCH₂Cl | 100 | 0 | 0 | 0 | 0 | 0 | 5 | 5 | 5 | 5 |
| | | 200 | 0 | 0 | 0 | 0 | 0 | 5 | 5 | 5 | 5 |
| | | 400 | 0 | 0 | 0 | 0 | 0 | 5 | 5 | 5 | 5 |

TABLE 5-continued

| No. | Compound | Dosage g/10a | Phytotoxicity to crops | | | | | Herbicidal activity | | | |
|---|---|---|---|---|---|---|---|---|---|---|---|
| | | | Rice | Wheat | Corn | Soybean | Cotton | Barnyard grass | Large crabgrass | Green foxtail | Yellowcyperus |
| 25 | [structure: 3-Cl-thiophene-CH(CH₃)-N(COCH₂Cl)-(2-OCH₃,6-CH₃-phenyl)] | 100 | 0 | 0 | 0 | 0 | 0 | 5 | 5 | 5 | 5 |
| | | 200 | 0 | 0 | 0 | 0 | 0 | 5 | 5 | 5 | 5 |
| | | 400 | 0 | 0 | 0 | 0 | 0 | 5 | 5 | 5 | 5 |
| 26 | [structure: 3-CH₂OCH₃-thiophene-CH(CH₃)-N(COCH₂Cl)-(3,5-diCH₃-phenyl)] | 100 | 0 | 0 | 0 | 0 | 0 | 5 | 5 | 4 | 5 |
| | | 200 | 0 | 0 | 0 | 0 | 0 | 5 | 5 | 5 | 5 |
| | | 400 | 0 | 0 | 0 | 0 | 0 | 5 | 5 | 5 | 5 |
| 27 | [structure: 5-Br-thiophene-CH(CH₃)-N(COCH₂Cl)-(2,6-diC₂H₅-phenyl)] | 100 | 0 | 0 | 0 | 0 | 0 | 5 | 4 | 4 | 5 |
| | | 200 | 0 | 0 | 0 | 0 | 0 | 5 | 5 | 5 | 5 |
| | | 400 | 0 | 0 | 0 | 0 | 0 | 5 | 5 | 5 | 5 |
| 28 | [structure: thiophene-CH₂-N(COCH₂Cl)-(2-CH₃,6-C₂H₅-phenyl)] | 100 | 0 | 0 | 0 | 0 | 0 | 3 | 2 | 1 | 3 |
| | | 200 | 2 | 1 | 0 | 0 | 0 | 3 | 3 | 3 | 4 |
| | | 400 | 3 | 3 | 2 | 0 | 0 | 4 | 4 | 4 | 5 |
| 29 | [structure: 3-CH₃-thiophene-CH₂-N(COCH₂Cl)-(2,6-diCH₃-phenyl)] | 100 | 1 | 1 | 0 | 0 | 0 | 3 | 3 | 1 | 4 |
| | | 200 | 3 | 2 | 1 | 0 | 0 | 4 | 3 | 3 | 4 |
| | | 400 | 4 | 3 | 2 | 1 | 3 | 4 | 4 | 3 | 5 |
| 30 | [structure: 5-NO₂-thiophene-CH₂-N(COCH₂Cl)-(2,6-diC₂H₅-phenyl)] | 100 | 0 | 0 | 0 | 0 | 0 | 0 | 0 | 0 | 0 |
| | | 200 | 0 | 0 | 0 | 0 | 0 | 0 | 0 | 0 | 0 |
| | | 400 | 0 | 0 | 0 | 0 | 0 | 0 | 0 | 0 | 0 |

TABLE 5-continued

| No. | Compound | Dosage g/10a | Phytotoxicity to crops ||||| Herbicidal activity ||||
|---|---|---|---|---|---|---|---|---|---|---|---|
| | | | Rice | Wheat | Corn | Soybean | Cotton | Barnyard grass | Large crabgrass | Green foxtail | Yellow-cyperus |
| 31 | 2-thienyl-CH₂–N(2,6-diMe-C₆H₃)(COCH₂Cl) | 100 | 2 | 2 | 0 | 0 | 0 | 3 | 3 | 3 | 3 |
| | | 200 | 3 | 3 | 0 | 0 | 0 | 4 | 3 | 4 | 4 |
| | | 400 | 4 | 4 | 2 | 1 | 0 | 5 | 5 | 5 | 5 |
| 32 | 2-thienyl-CH₂–N(2,6-diEt-C₆H₃)(COCH₂Cl) | 100 | 1 | 0 | 0 | 0 | 0 | 3 | 2 | 2 | 3 |
| | | 200 | 2 | 1 | 0 | 0 | 0 | 4 | 3 | 3 | 4 |
| | | 400 | 3 | 3 | 1 | 0 | 0 | 4 | 4 | 4 | 4 |
| 33 | H₃COCH₂–N(2,6-diEt-C₆H₃)(COCH₂Cl) | 100 | 5 | 4 | 0 | 0 | 0 | 5 | 5 | 5 | 3 |
| | | 200 | 5 | 5 | 2 | 0 | 1 | 5 | 5 | 5 | 4 |
| | | 400 | 5 | 5 | 3 | 1 | 2 | 5 | 5 | 5 | 4 |

EXAMPLE 10

Porcelain pots (1/8850 a) were filled with upland farm soil (clay loam), and seeds of the plants shown in Table 6 were sown to a depth of 0.5 to 1 cm. An aqueous dilution of a wettable powder of each of the test compounds, prepared as in Formuation Example 1, was sprayed in a predetermined amount over the stalks and leaves of the plants. After the treatment, the plants were allowed to grow in a greenhouse. Twe weeks later, the herbicidal effects of the test compounds were examined. The results are shown in Table 6 together with those obtained with comparative compounds (Nos. 28 to 32). The phytotoxicity to crops and the herbicidal effects were rated on the same scales as in Example 7.

TABLE 6

| No. | Compound | Dosage g/10a | Phytotoxicity to crops ||||| Herbicidal activity |||
|---|---|---|---|---|---|---|---|---|---|---|
| | | | Rice | Wheat | Corn | Soybean | Cotton | Barnyard grass | Large crabgrass | Green foxtail |
| 1 | 5-Cl-2-thienyl-CH₂–N(2,6-diMe-C₆H₃)(COCH₂Cl) | 200 | 0 | 0 | 0 | 0 | 0 | 5 | 4 | 3 |
| | | 400 | 0 | 0 | 0 | 0 | 0 | 5 | 5 | 4 |
| | | 800 | 0 | 0 | 0 | 0 | 0 | 5 | 5 | 5 |
| 2 | 3-Cl-2-thienyl-CH₂–N(2,6-diMe-C₆H₃)(COCH₂Cl) | 200 | 0 | 0 | 0 | 0 | 0 | 5 | 5 | 4 |
| | | 400 | 0 | 0 | 0 | 0 | 0 | 5 | 5 | 5 |
| | | 800 | 0 | 2 | 0 | 0 | 0 | 5 | 5 | 5 |

TABLE 6-continued

| No. | Compound | Dosage g/10a | Phytotoxicity to crops | | | | | Herbicidal activity | | |
|---|---|---|---|---|---|---|---|---|---|---|
| | | | Rice | Wheat | Corn | Soy-bean | Cotton | Barnyard grass | Large crabgrass | Green foxtail |
| 3 | 4-Br-thienyl-CH₂-N(COCH₂Cl)-(2-OCH₃-6-CH₃-phenyl) | 200 | 0 | 0 | 0 | 0 | 0 | 5 | 4 | 3 |
| | | 400 | 0 | 0 | 0 | 0 | 0 | 5 | 5 | 3 |
| | | 800 | 0 | 0 | 0 | 0 | 0 | 5 | 5 | 4 |
| 4 | 3-SCH₃-thienyl-CH₂-N(COCH₂Cl)-(2,6-di-CH₃-phenyl) | 200 | 0 | 0 | 0 | 0 | 0 | 5 | 5 | 3 |
| | | 400 | 0 | 0 | 0 | 0 | 0 | 5 | 5 | 4 |
| | | 800 | 0 | 0 | 0 | 0 | 0 | 5 | 5 | 5 |
| 5 | 3-OCH₃-thienyl-CH₂-N(COCH₂Cl)-(3,5-di-CH₃-phenyl) | 200 | 0 | 0 | 0 | 0 | 0 | 4 | 3 | 4 |
| | | 400 | 0 | 0 | 0 | 0 | 0 | 4 | 4 | 4 |
| | | 800 | 0 | 0 | 0 | 0 | 0 | 5 | 5 | 5 |
| 6 | 3-OCH₃-thienyl-CH₂-N(COCH₂Cl)-(2-OCH₃-6-CH₃-phenyl) | 200 | 0 | 0 | 0 | 0 | 0 | 5 | 5 | 5 |
| | | 400 | 0 | 0 | 0 | 0 | 0 | 5 | 5 | 5 |
| | | 800 | 0 | 2 | 0 | 0 | 0 | 5 | 5 | 5 |
| 7 | 3-OCH₃-thienyl-CH₂-N(COCH₂Cl)-(2,6-di-CH₃-phenyl) | 200 | 0 | 0 | 0 | 0 | 0 | 5 | 5 | 4 |
| | | 400 | 0 | 1 | 0 | 0 | 0 | 5 | 5 | 5 |
| | | 800 | 0 | 2 | 0 | 0 | 0 | 5 | 5 | 5 |
| 8 | 3-Cl-thienyl-CH₂-N(COCH₂Cl)-(2-OCH₃-6-CH₃-phenyl) | 200 | 0 | 0 | 0 | 0 | 0 | 5 | 4 | 4 |
| | | 400 | 0 | 0 | 0 | 0 | 0 | 5 | 5 | 5 |
| | | 800 | 0 | 1 | 0 | 0 | 0 | 5 | 5 | 5 |
| 9 | 5-H₃CO-thienyl-CH₂-N(COCH₂Cl)-(2,6-di-CH₃-phenyl) | 200 | 0 | 0 | 0 | 0 | 0 | 5 | 4 | 3 |
| | | 400 | 0 | 0 | 0 | 0 | 0 | 5 | 5 | 5 |
| | | 800 | 0 | 0 | 0 | 0 | 0 | 5 | 5 | 5 |

TABLE 6-continued

| No. | Compound | Dosage g/10a | Phytotoxicity to crops ||||| Herbicidal activity |||
|---|---|---|---|---|---|---|---|---|---|---|
| | | | Rice | Wheat | Corn | Soy-bean | Cotton | Barnyard grass | Large crabgrass | Green foxtail |
| 10 | [thiophene-OCH₃, CH₂-N(2,6-diMe-C₆H₃... C₂H₅)COCH₂Cl] | 200 | 0 | 0 | 0 | 0 | 0 | 5 | 4 | 3 |
| | | 400 | 0 | 0 | 0 | 0 | 0 | 5 | 5 | 3 |
| | | 800 | 0 | 0 | 0 | 0 | 0 | 5 | 5 | 5 |
| 11 | [thiophene-OCH₃, CH₂-N(2-Cl-6-Me-C₆H₃)COCH₂Cl] | 200 | 0 | 0 | 0 | 0 | 0 | 5 | 5 | 5 |
| | | 400 | 0 | 2 | 0 | 0 | 0 | 5 | 5 | 5 |
| | | 800 | 0 | 2 | 0 | 0 | 0 | 5 | 5 | 5 |
| 12 | [CH₃OCH₂-thiophene-CH₂-N(2,6-diMe-C₆H₃)COCH₂Cl] | 200 | 0 | 0 | 0 | 0 | 0 | 5 | 4 | 5 |
| | | 400 | 0 | 0 | 0 | 0 | 0 | 5 | 5 | 5 |
| | | 800 | 0 | 0 | 0 | 0 | 0 | 5 | 5 | 5 |
| 13 | [thiophene-CH₂OCH₃, CH₂-N(2,6-diMe-C₆H₃)COCH₂Cl] | 200 | 0 | 0 | 0 | 0 | 0 | 5 | 4 | 4 |
| | | 400 | 0 | 0 | 0 | 0 | 0 | 5 | 5 | 5 |
| | | 800 | 0 | 0 | 0 | 0 | 0 | 5 | 5 | 5 |
| 14 | [thiophene-SCH₃, CH₂-N(2-Me-6-... C₂H₅)COCH₂Cl] | 200 | 0 | 0 | 0 | 0 | 0 | 4 | 4 | 3 |
| | | 400 | 0 | 0 | 0 | 0 | 0 | 5 | 5 | 5 |
| | | 800 | 0 | 0 | 0 | 0 | 0 | 5 | 5 | 5 |
| 15 | [thiophene-SCH₃, CH₂-N(2,6-diEt-C₆H₃)COCH₂Cl] | 200 | 0 | 0 | 0 | 0 | 0 | 4 | 4 | 3 |
| | | 400 | 0 | 0 | 0 | 0 | 0 | 5 | 4 | 4 |
| | | 800 | 0 | 0 | 0 | 0 | 0 | 5 | 5 | 4 |
| 16 | [thiophene-SC₂H₅, CH₂-N(2,6-diMe-C₆H₃)COCH₂Cl] | 200 | 0 | 0 | 0 | 0 | 0 | 3 | 3 | 3 |
| | | 400 | 0 | 0 | 0 | 0 | 0 | 5 | 4 | 3 |
| | | 800 | 0 | 0 | 0 | 0 | 0 | 5 | 4 | 3 |

TABLE 6-continued

| No. | Compound | Dosage g/10a | Phytotoxicity to crops | | | | | Herbicidal activity | | |
|---|---|---|---|---|---|---|---|---|---|---|
| | | | Rice | Wheat | Corn | Soy-bean | Cotton | Barnyard grass | Large crabgrass | Green foxtail |
| 17 | 3,4-dichlorothiophene-CH2-N(2,6-dimethylphenyl)(COCH2Cl) | 200 | 0 | 0 | 0 | 0 | 0 | 3 | 2 | 1 |
| | | 400 | 0 | 0 | 0 | 0 | 0 | 3 | 3 | 3 |
| | | 800 | 0 | 0 | 0 | 0 | 0 | 4 | 4 | 3 |
| 18 | 4,5-dibromothiophene-CH2-N(2,6-dimethylphenyl)(COCH2Cl) | 200 | 0 | 0 | 0 | 0 | 0 | 3 | 2 | 2 |
| | | 400 | 0 | 0 | 0 | 0 | 0 | 3 | 3 | 3 |
| | | 800 | 0 | 0 | 0 | 0 | 0 | 3 | 4 | 4 |
| 19 | 3,4-dimethoxythiophene-CH2-N(2,6-diethylphenyl)(COCH2Cl) | 200 | 0 | 0 | 0 | 0 | 0 | 3 | 3 | 3 |
| | | 400 | 0 | 0 | 0 | 0 | 0 | 4 | 4 | 3 |
| | | 800 | 0 | 0 | 0 | 0 | 0 | 5 | 5 | 4 |
| 20 | 5-iodothiophene-CH2-N(2,6-dimethylphenyl)(COCH2Cl) | 200 | 0 | 0 | 0 | 0 | 0 | 2 | 2 | 1 |
| | | 400 | 0 | 0 | 0 | 0 | 0 | 3 | 3 | 3 |
| | | 800 | 0 | 0 | 0 | 0 | 0 | 3 | 4 | 3 |
| 21 | 3,4-dichlorothiophene-CH2-N(2,6-diethylphenyl)(COCH2Cl) | 200 | 0 | 0 | 0 | 0 | 0 | 3 | 1 | 0 |
| | | 400 | 0 | 0 | 0 | 0 | 0 | 4 | 3 | 2 |
| | | 800 | 0 | 0 | 0 | 0 | 0 | 4 | 3 | 3 |
| 22 | 4-bromothiophene-CH2-N(2,6-dimethylphenyl)(COCH2Cl) | 200 | 0 | 0 | 0 | 0 | 0 | 5 | 5 | 5 |
| | | 400 | 0 | 0 | 0 | 0 | 0 | 5 | 5 | 5 |
| | | 800 | 0 | 0 | 0 | 0 | 0 | 5 | 5 | 5 |
| 23 | 5-chlorothiophene-CH(CH3)-N(2-methylphenyl)(COCH2Cl) | 200 | 0 | 0 | 0 | 0 | 0 | 5 | 5 | 5 |
| | | 400 | 0 | 0 | 0 | 0 | 0 | 5 | 5 | 5 |
| | | 800 | 0 | 0 | 0 | 0 | 0 | 5 | 5 | 5 |

TABLE 6-continued

| No. | Compound | Dosage g/10a | Phytotoxicity to crops | | | | | Herbicidal activity | | |
|---|---|---|---|---|---|---|---|---|---|---|
| | | | Rice | Wheat | Corn | Soybean | Cotton | Barnyard grass | Large crabgrass | Green foxtail |
| 24 | [3-OCH₃-thienyl-CH(CH₃)-N(2,6-diMe-C₆H₃)(COCH₂Cl)] | 200 | 0 | 0 | 0 | 0 | 0 | 5 | 5 | 5 |
| | | 400 | 0 | 0 | 0 | 0 | 0 | 5 | 5 | 5 |
| | | 800 | 0 | 0 | 0 | 0 | 0 | 5 | 5 | 5 |
| 25 | [3-Cl-thienyl-CH(CH₃)-N(2-OCH₃-6-CH₃-C₆H₃)(COCH₂Cl)] | 200 | 0 | 0 | 0 | 0 | 0 | 5 | 5 | 5 |
| | | 400 | 0 | 0 | 0 | 0 | 0 | 5 | 5 | 5 |
| | | 800 | 0 | 0 | 0 | 0 | 0 | 5 | 5 | 5 |
| 26 | [3-CH₂OCH₃-thienyl-CH(CH₃)-N(3,5-diMe-C₆H₃)(COCH₂Cl)] | 200 | 0 | 0 | 0 | 0 | 0 | 5 | 5 | 4 |
| | | 400 | 0 | 0 | 0 | 0 | 0 | 5 | 5 | 5 |
| | | 800 | 0 | 0 | 0 | 0 | 0 | 5 | 5 | 5 |
| 27 | [5-Br-thienyl-CH(CH₃)-N(2,6-diEt-C₆H₃)(COCH₂Cl)] | 200 | 0 | 0 | 0 | 0 | 0 | 5 | 3 | 4 |
| | | 400 | 0 | 0 | 0 | 0 | 0 | 5 | 5 | 5 |
| | | 800 | 0 | 0 | 0 | 0 | 0 | 5 | 5 | 5 |
| 28 | [3-CH₃-thienyl-CH₂-N(2,6-diMe-C₆H₃)(COCH₂Cl)] | 200 | 4 | 3 | 0 | 0 | 0 | 3 | 2 | 1 |
| | | 400 | 4 | 4 | 1 | 0 | 1 | 3 | 3 | 2 |
| | | 800 | 4 | 4 | 3 | 2 | 2 | 4 | 3 | 3 |
| 29 | [5-NO₂-thienyl-CH₂-N(2,6-diEt-C₆H₃)(COCH₂Cl)] | 200 | 0 | 0 | 0 | 0 | 0 | 0 | 0 | 0 |
| | | 400 | 0 | 0 | 0 | 0 | 0 | 0 | 0 | 0 |
| | | 800 | 0 | 0 | 0 | 0 | 0 | 0 | 0 | 0 |
| 30 | [thienyl-CH₂-N(2-CH₃-6-C₂H₅-C₆H₃)(COCH₂Cl)] | 200 | 2 | 2 | 0 | 0 | 0 | 3 | 2 | 1 |
| | | 400 | 4 | 3 | 0 | 0 | 0 | 4 | 3 | 2 |
| | | 800 | 5 | 4 | 2 | 1 | 0 | 4 | 3 | 3 |

TABLE 6-continued

| No. | Compound | Dosage g/10a | Phytotoxicity to crops | | | | | Herbicidal activity | | |
|---|---|---|---|---|---|---|---|---|---|---|
| | | | Rice | Wheat | Corn | Soybean | Cotton | Barnyard grass | Large crabgrass | Green foxtail |
| 31 | 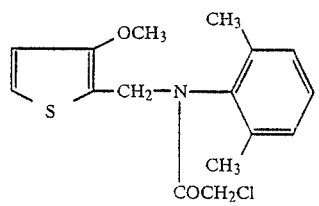 | 200 | 3 | 1 | 0 | 0 | 0 | 3 | 3 | 3 |
| | | 400 | 4 | 3 | 0 | 0 | 0 | 4 | 4 | 3 |
| | | 800 | 5 | 4 | 2 | 0 | 0 | 5 | 5 | 5 |
| 32 | 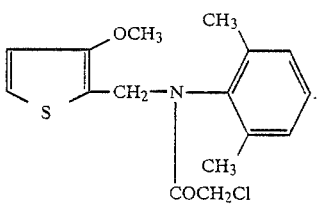 | 200 | 1 | 1 | 0 | 0 | 0 | 3 | 2 | 0 |
| | | 400 | 3 | 2 | 0 | 0 | 0 | 3 | 3 | 2 |
| | | 800 | 3 | 3 | 1 | 0 | 0 | 4 | 3 | 3 |

What we claim is:

1. A herbicidal composition comprising a herbicidally effective amount of an N-substituted chloroacetanilide represented by the following formula and a herbicidally acceptable diluent or carrier.

2. The herbicidal composition of claim 1 which comprises from about 0.01 to 95% by weight, based on the weight of the entire composition, of the N-substituted chloroacetanilide compound.

3. A method of controlling paddy weeds, which comprises applying to a paddy at a rate of about 1.5 to about 2,000 g per 10a an N-substituted chloroacetanilide compound of the formula 4. The method of claim 3 wherein the application ray is from about 15 to about 500 g per 10a.

* * * * *

UNITED STATES PATENT AND TRADEMARK OFFICE
CERTIFICATE OF CORRECTION

PATENT NO. : 4,802,907
DATED : February 7, 1989
INVENTOR(S) : Takematsu, et al.

It is certified that error appears in the above-identified patent and that said Letters Patent is hereby corrected as shown below:

On the face of the patent, under "Foreign Application Priority Data", change the Japanese application number from "58-111011" to read --58-111077--.

Signed and Sealed this

Twenty-first Day of November, 1989

*Attest:*

JEFFREY M. SAMUELS

*Attesting Officer*     *Acting Commissioner of Patents and Trademarks*